(12) United States Patent
Arnone et al.

(10) Patent No.: US 6,388,799 B1
(45) Date of Patent: May 14, 2002

(54) OPTICAL DEVICE AND IMAGING SYSTEM

(75) Inventors: Donald Dominic Arnone; Andrew James Shields; Richard Andrew Hogg; Craig Michael Ciesla; David Mark Whittaker; Edmund Harold Linfield; Alexander Giles Davies, all of Cambridge (GB)

(73) Assignee: Toshiba Research Europe Limited, Cambridge (GB)

( * ) Notice: Subject to any disclaimer, the term of this patent is extended or adjusted under 35 U.S.C. 154(b) by 0 days.

(21) Appl. No.: 09/432,762

(22) Filed: Nov. 3, 1999

(30) Foreign Application Priority Data

Nov. 3, 1998 (GB) ............................................. 9824058
Feb. 12, 1999 (GB) ............................................. 9903307

(51) Int. Cl.[7] .......................... G02F 01/35; H01S 03/10
(52) U.S. Cl. ........................................ 359/326; 372/20
(58) Field of Search ................................ 359/326, 332; 372/3, 20, 22

(56) References Cited

U.S. PATENT DOCUMENTS

| | | | |
|---|---|---|---|
| 5,345,457 A | | 9/1994 | Zenzie et al. ................. 372/22 |
| 5,633,883 A | | 5/1997 | Shi et al. ...................... 372/20 |
| 5,673,281 A | | 9/1997 | Byer ............................. 372/3 |
| 5,734,494 A | * | 3/1998 | Xu et al. ...................... 359/332 |
| 5,789,750 A | * | 8/1998 | Nuss ......................... 250/338.1 |
| 5,802,086 A | | 9/1998 | Hargis et al. ................. 372/22 |
| 5,912,912 A | * | 6/1999 | Caprara et al. ............... 372/25 |
| 5,930,030 A | * | 7/1999 | Scifres ........................ 359/341 |
| 6,009,110 A | * | 12/1999 | Wiechmann et al. ......... 372/10 |
| 6,304,237 B1 | * | 10/2001 | Karakawa .................... 345/84 |

FOREIGN PATENT DOCUMENTS

| | | | |
|---|---|---|---|
| EP | 0 439 350 | * | 7/1991 |
| EP | 0 485 187 | * | 5/1992 |
| EP | 0 486 192 | * | 5/1992 |
| EP | 0 753 767 | * | 1/1997 |
| EP | 0 788 015 | * | 8/1997 |
| WO | WO 90/04867 | * | 5/1990 |
| WO | WO 94/23335 | * | 10/1994 |

OTHER PUBLICATIONS

M.W. Street, et al., Appl. Phys. Lett., vol. 70, No. 21, pp. 2804–2806, "Modification of the Second–Order Optical Nonlinearities in AlGaAs Asymmetric Multiple Quantum Well Waveguides by Quantum Well Intermixing," May 26, 1997.*
A. Flore, et al., Nature, vol. 391, No. 29, pp. 463–466, "Phase Matching Using an Isotropic Nonlinear Optical Material," Jan. 1998.*
V. Petrov, et al., Optical Letters, vol. 19, No. 1, pp. 40–42, "Intracavity Difference–Frequency Generation of Near–Infrared Picosecond Pulses in a Synchronously Mode–Locked CW Dye Laser," Jan. 1, 1994.*
N. Sarukura, et al., Jpn, J. Appl. Phys., vol. 36, No. 5A, pp. 560–562, "All–Solid–State, THz Radiation Source Using a Saturable Bragg Reflector in a Femtosecond Mode–Locked Laser," May 1, 1997.*

* cited by examiner

Primary Examiner—Ricky Mack
(74) Attorney, Agent, or Firm—Oblon, Spivak, McClelland, Maier & Neustadt, P.C.

(57) ABSTRACT

An optical device for efficient radiation emission having a modulation region with phase matching means (1) for enhancing the phase matching between two different frequency signals propagating in the optical modulation region (1) in response to illumination by at least one incident beam (7, 8), the phase matching means (1), having a spatial variation in its refractive index (5) along the path of the incident radiation beam (7, 8). The device may be configured as a radiation source comprising a frequency conversion member (C2) for emitting a beam of radiation (553) in response to irradiation by one or more input beams (507), the emitted beam (553) having a frequency different to that of the one or more input beams (507), the one or more input beams (507) all being produced within a lasing cavity (defined by M3, M4, M5, M6 and output coupler (523)) and said frequency conversion member (C2) being located within said lasing cavity. The invention also extends to an imaging system using the radiation source.

56 Claims, 24 Drawing Sheets

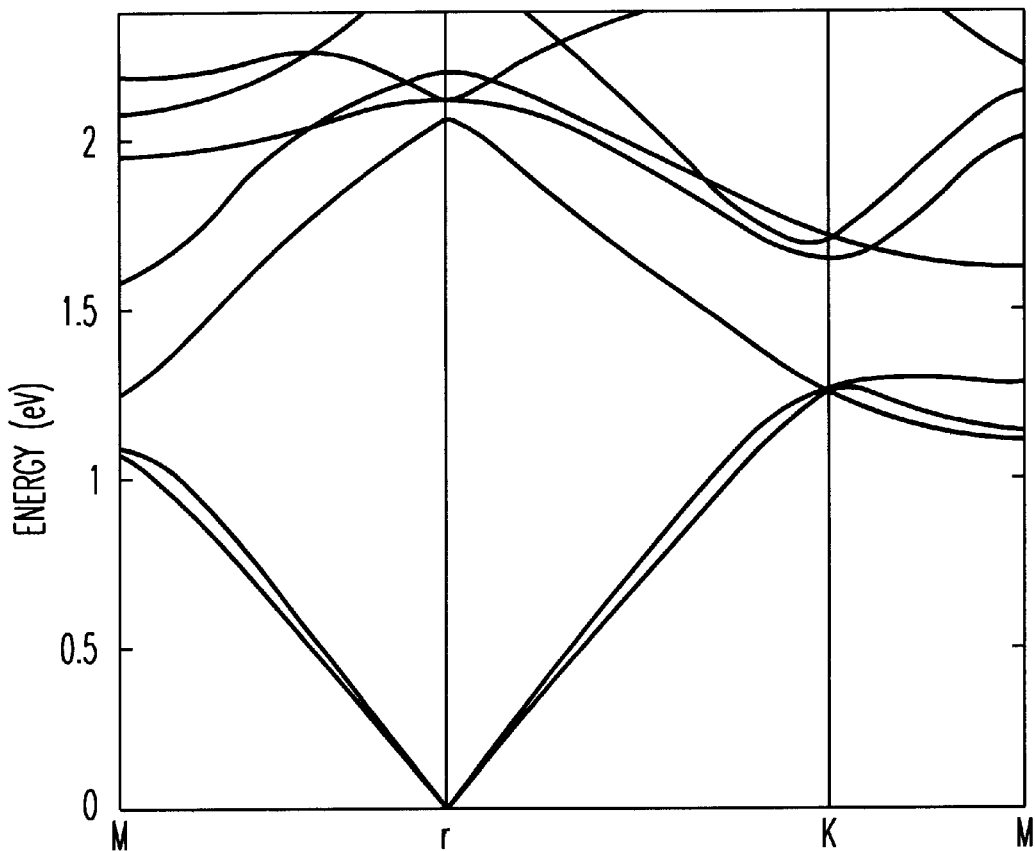
FIG. 19
BULK GEOMETRY
TRIANGULAR LATTICE
LATTICE CONSTANT=200nm
CIRCULAR HOLES
FILL FACTOR=0.27
HOLE RADIUS=54.6nm
EXTERNAL INDEX=3.5
INTERNAL INDEX=1.0
$-8 < n_1 < 8$
$-8 < n_2 < 8$
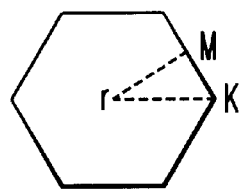

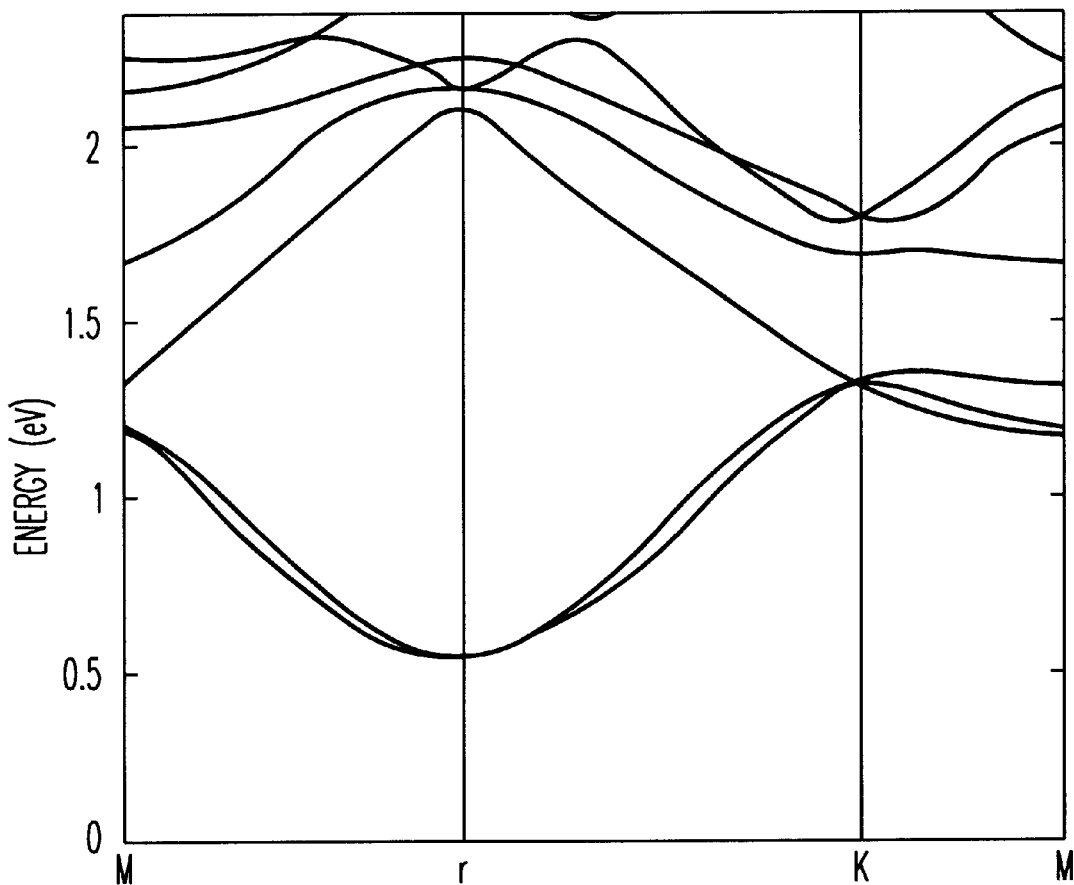
FIG. 20
WAVEGUIDE GEOMETRY
GUIDE THICKNESS=400nm
TRIANGULAR LATTICE
LATTICE CONSTANT=200nm
CIRCULAR HOLES
FILL FACTOR=0.27
HOLE RADIUS=54.6nm
EXTERNAL INDEX=3.5
INTERNAL INDEX=1.0
$-8 < n_1 < 8$
$-8 < n_2 < 8$
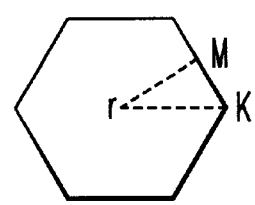
LOWEST GUIDED MODE

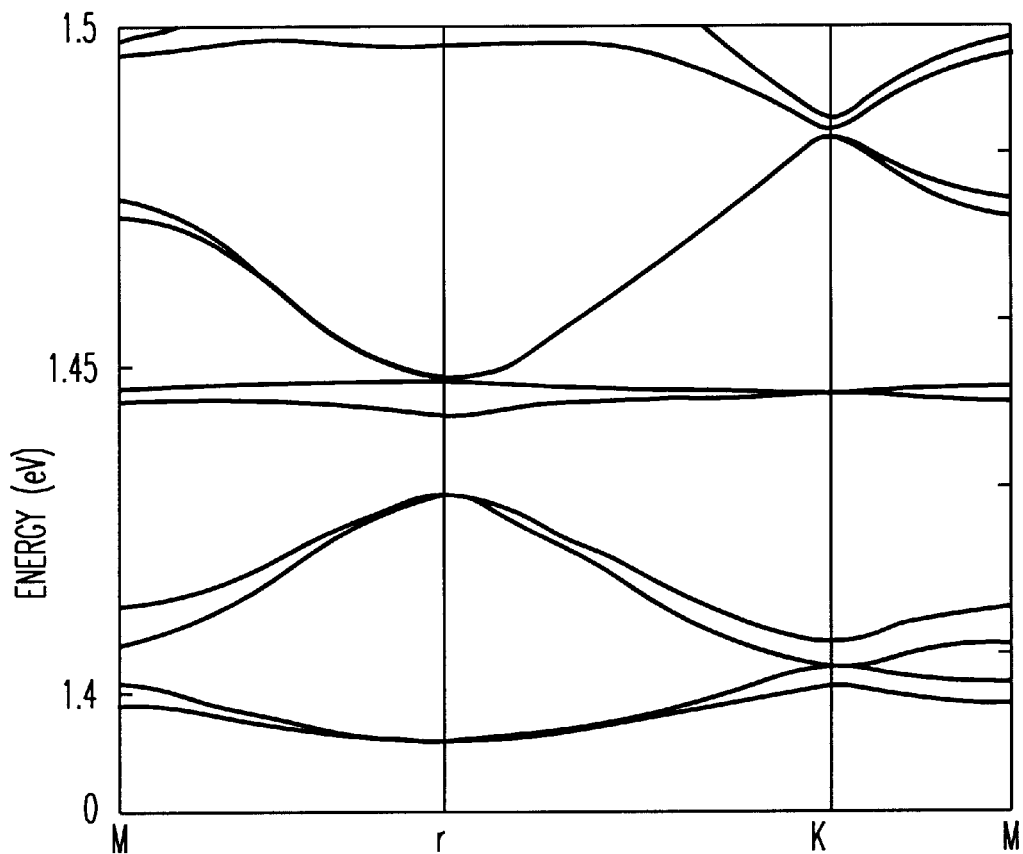
FIG. 21
WAVEGUIDE GEOMETRY
GUIDE THICKNESS=130nm
TRIANGULAR LATTICE
LATTICE CONSTANT=1000nm
CIRCULAR HOLES
FILL FACTOR=0.27
HOLE RADIUS=272.8nm
EXTERNAL INDEX=3.5
INTERNAL INDEX=1.0
$-8 < n_1 < 8$
$-8 < n_2 < 8$
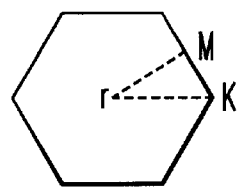

OPTICAL DEVICE AND IMAGING SYSTEM

FIELD OF INVENTION

The present invention relates to the field of optical devices such as radiation sources and detectors. More specifically, the present invention relates to optical devices used to efficiently generate a beam of radiation with a given frequency or within a band of frequencies. The present invention may also extend to an imaging system.

BACKGROUND OF INVENTION

Difficulties arise in producing electromagnetic radiation in several commercially important wavelength bands. For instance, in the terahertz (THz) frequency range (100 Ghz to 20 THz), near and mid-infra red (wavelength=1000–5000 nm) and blue/UV (wavelength=400–450 nm).

A possible method of producing such frequencies is to use non linear optical effects. The polarisation P in the material induced by the incident radiation can be expressed in terms of E the electric field exciting the material as the power series:

$$P = \chi_1 E + \chi_2 E^2 + \chi_3 E^3 \ldots$$

Generally, the relationship P∝E is used and the higher order terms are assumed to be negligibly small. This approximation does not hold for large E. Non linear optics is concerned with these higher order terms.

If a material is irradiated with two different frequencies, the second order term allows the material to emit frequencies which are the sum of the input frequencies (known as Sum Frequency Generation), the difference between the input frequencies (Difference Frequency Generation) The second order susceptibility can also result in the generation of different optical frequencies when the material is irradiated by a single input frequency. For instance, second harmonic generation results from self sum generation. For optical parametric conversion, two frequencies are generated from the input frequency.

Also, the third order term $\chi_3 E^3$ can also be excited to produce third harmonic frequencies and other third order terms.

The problem which arises in such structures is that to obtain emitted radiation with the desired frequency efficiently, the phase of the polarisation induced by the incident radiation needs to be matched as closely as possible to the phase of the desired emitted radiation.

This phase matching problem also arises in certain types of detectors where changes in a reference beam with a first frequency due to a beam with a second frequency are used to measure the beam with the second frequency.

Some materials have a natural degree of phase matching due to birefringence properties and hence phase matching can be achieved over at least a certain length of the material. However, many materials with large optical non linearities nevertheless suffer from having no birefringence or other properties which allow some degree of phase matching and thus the full realisation of the material as a frequency converter.

SUMMARY OF THE INVENTION

The present invention addresses the above problems and in a first aspect, provides an optical device comprising an optical modulation region which comprises phase matching means for enhancing the phase matching between at least two different frequency signals propagating in the optical modulation region in response to illumination by at least one incident beam of radiation, the phase matching means having a spatial variation in its refractive index along a component of the incident radiation beam configured to maximise a distance in the modulation region over which the at least two different frequency signals stay in phase.

To clarify the above, a component of the incident radiation beam is a directional component of the beam.

If the present invention is used for frequency conversion, the optical modulation region preferably comprises frequency conversion means for emitting a beam with an emitted radiation frequency in response to illumination with the at least one incident beam of radiation, the phase matching means enhancing the phase matching between the polarisation generated by the or an incident beam and the emitted beam. The emitted beam having a different frequency to that of the incident beam.

There are many possible mechanisms for converting the frequency of the input radiation.

A new frequency can be generated from incident radiation with two or more frequencies, by so called sum or difference frequency generation.

The optical device is illuminated with radiation which either has two frequency components or the device is illuminated with two beams of radiation of different frequencies.

The higher fields obtainable by pulsed lasers allow the (progressively smaller) non linearities in the polarisation term to be accessed.

Preferably, a pulsed laser is used in order to generate the two incident frequencies. Also, the radiation pulse, produced by a pulsed laser inherently contains a number of different frequencies making it ideal for sum or difference frequency generation over a broad range.

However, with the enhanced phase matching achievable with the present invention, lower fields can be used and hence the two frequencies could be provided by two CW lasers operating at different frequencies. These provide a continuous beam which does not provide as high an electric field as a pulsed system although non-linear effects still may be accessed with CW lasers. CW lasers also have the advantage that they are presently more ubiquitous and commercially available than pulsed lasers.

The incident radiation generates a time-dependent polarisation via the second order non linearity of the material. A simplified view of the mechanism is to picture the electrons in the material as being on springs. The incident radiation causes the electrons to vibrate with frequencies corresponding to the incident frequencies, their sum and their difference.

Which frequency is emitted is dependent on the non-linear coefficients of the material at the fundamental frequency, and phase matching between the non-linear polarisation and generated/converted radiation at the sum/difference frequencies.

For sum frequency generation, the phase matching condition is given by $$\Delta k = k(\omega_1) + k(\omega_2) - k(\omega_3) = 0,$$

where $\omega_1 + \omega_2 = \omega_3$ and $k(\omega)$ is the k-vector of the light in the material at frequency $\omega$. For difference frequency generation the phase matching condition is given by $$\Delta k = k(\omega_1) - k(\omega_2) - k(\omega_3) = 0$$

where $\omega_1 - \omega_2 = \omega_3$.

For Nth harmonic generation the phase matching condition is given by $$\Delta k = Nk(\omega_1) - k(\omega_2) = 0$$

where N $\omega_1 = \omega_2$.

For optical parametric generation the phase matching condition is given by $$\Delta k = k(\omega_1) - k(\omega_2) - k(\omega_3) = 0$$

where $\omega_1 = \omega_2 + \omega_3$.

The coherence length, which can be thought of as the distance over which the generated field becomes out of phase with the driving field, is defined as $$l_c = 2/\Delta k$$

The refractive index, n, of the material is defined by n=kc/$\omega$, where c is the speed of light in vacuum. Since the refractive index of many non-linear materials varies with the frequency $\omega$, the coherence length is typically just a few microns. The present invention modifies the dispersion, i.e. the variation of n with $\omega$, in order to satisfy the phase matching condition $\Delta k = 0$.

Considering the case where THz radiation with a frequency $\omega_{THz}$ is generated from two visible radiation frequencies $\omega_{opt}$ using the technique of difference frequency generation. Phase matching for the generating THz radiation from the difference between the frequencies of the incident radiation is:

$$\Delta k = k(\omega_{opt} + \omega_{THz}) - k(\omega_{opt}) - k(\omega_{THz}) = 0.$$

The coherence length, $l_c$, which is a measure of the distance over which the optically-induced non-linear polarisation and the generated THz electric fields remain in phase, is defined:

$$l_c = \pi c / (\omega_{THz} |\eta_{vis} - \eta_{THz}|)$$

where $\eta_{vis}$ is the refractive index of the material at visible frequencies and $\eta_{THz}$ is the refractive index of the material at THz frequencies, Thus, for the long coherence length necessary for efficient THz generation, $\eta_{vis} - \eta_{THz}$ must be small. However, inorganic non-linear optical materials have a large index mismatch and so $l_c$ may be no larger than a few microns.

The present invention enhances the phase matching by reducing this variation in the refractive indices at the different frequencies.

Similarly, the modulation region can be configured such that the second order coefficient of the addition of the two frequencies is more efficiently emitted. Alternatively, the second harmonic can be selected instead.

A further possible mode of operation is by optical parametric generation. The optical device is pumped by a single laser.

Due to the non-linear character of the material, two beams with different frequencies can be emitted or the second harmonic can be emitted.

The two different frequencies are related to the input frequency by momentum and energy conservation.

The above devices can be supplied by radiation from one or two diode lasers. Therefore, the laser and the optical device can be integrated together on a single chip Also, a pulse laser can be integrated on a single chip with the frequency converter.

The above phase matching principles can also be applied to detectors, in this case, the modulation region is preferably configured to rotate the polarisation vector of a first input beam in response to illumination with a second input beam and emit a beam with the rotated polarisation vector, The first input beam can be thought of as a reference beam, the second beam is the detected beam. Before entering the detector, the polarisation of the reference beam and the detected beam are rotated such that they are parallel to one another and have a component along both the ordinary and extraordinary axes of the modulation region.

The reference beam and the detected beam are preferably linearly polarised before entering the optical modulator. However, one or both of them may also be circularly polarised.

The modulation region is configured so that the detected beam (if present) rotates the polarisation of the reference beam by an angle. If the detected beam is not present, the reference beam may become slightly elliptically polarised during its passage through the optical modulation region. To compensate for this effect, the beam emitted from the modulation region is preferably passed through an optical correction circuit.

Preferably, the optical correction circuit converts the linearly (or elliptically) polarised beam into a circularly polarised beam, The emitted linearly (or elliptically) polarised beam is preferably converted into a circularly polarised beam by a quarter wave plate. Preferably, this circularly polarised beam is then passed into a polarisation splitting device (such as a Wollaston prism) which separates the circularly polarised radiation into two linear components. If the detected beam is not present, these linear components are equal. If the detected beam is present, these linear components are not equal to one another.

Preferably, the two output beams from the prism are incident on a balanced photodiode assembly, which produces a non-zero output signal if there is a difference in magnitude between the two beams.

Alternatively, the reference beam can be circularly polarised before entering the detector. This can be achieved by putting the quarter wave plate in the path of the reference beam before it reaches the detector. The detected beam (if present) changes the circularly polarised reference beam into an elliptically polarised beam. The elliptically polarised beam is then separated into its two components by a Wollaston prism or the like as described previously.

The optical device of the present invention can therefore be used in both the generation of radiation and the detection of radiation. Hence, an imaging system is provided which uses the present invention configured as a generator (frequency converter) to provide the imaging radiation and the present invention configured as a detector to detect the imaging radiation. It will be appreciated by a man skilled in the art that an imaging system can have either of the generator or the detector as described above coupled with a conversion detector or generator respectively.

Preferably a beam is split to form an input for the generator and a reference beam for the detector. Imaging radiation is produced by the generator to image a sample. The radiation carrying the image information is then detected by the detector using the reference beam. Preferably a control system is provided which provides a time variation between the input beam and the reference beam.

Possible materials which posses good non linear characteristics for any of the above mechanisms are GaAs or Si based semiconductors. More preferably, a crystalline structure is used. The following are further examples of possible materials: $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium).

In general, non-centrosymmetric crystals are used for second order effects. Third order effects are found in a variety of different crystals with varying strengths.

It is preferable if such a structure is placed in a waveguide configuration which operates at least one of the input beam frequencies. The waveguide can be realised by either a single cladding layer and a core layer or a core layer interposed between two cladding layers. For example, a GaAs layer interposed between AlGaAs cladding layers.

Ideally, the material has a periodic variation in its refractive index. Preferably, the refractive index will vary with a pitch of between 100 nm and 10 μm. More preferably between 0.5 μm and 5 μm.

The variation in the refractive index can be achieved in a number of ways. A simple method is to just etch holes into the non-linear optical material such that a local variation in the refractive index is caused within the path of the beam.

The holes can be formed in just the core layer, the core layer and one or both of the cladding layers or one or both of the cladding layers with no holes formed in the core layer. More complex structures could use two materials with different refractive indices. For example GaAs and AlGaAs. A first material with a first refractive index has holes or slots provided in it and the second material which has a different refractive index to the first material fills the holes or the slots of the first material.

The variation in the refractive index produces a variation in the component k-vector (momentum direction) along the direction in which the index varies or is modulated.

However, in practice, the beam might be perpendicular to an input surface of the modulation region such that the k-vector of the beam is parallel to the direction in which the refractive index varies for maximum effect. Alternatively, the beam may be incident at an angle to the input surface, say, for example, at 45°. In this case, only a component of the input beam's k-vector is parallel to the direction in which the variation in refractive index occurs, Such structures can be achieved by regrowth, ion beam implantation, ion beam lithography and standard lithographic patterning techniques. Preferably, such structures are provided with straight boundaries between the regions with different refractive indices.

It may be preferable in some cases to integrate a source for supplying the incident beam or beams with the optical modulation region. The source may be a single CW source (for parametric generation or second harmonic generation) or a pulsed laser source or two CW sources for sum and difference frequency generation.

The optical modulation region may be located within a mirror cavity. Further, the at least one incident beam of radiation may be produced within a lasing cavity and said optical modulation region may be provided within the said cavity.

In a second aspect, the present invention provides a radiation source comprising.

a frequency conversion member for emitting a beam of radiation in response to irradiation by one or more input beams, the emitted beam having a frequency different to that of the one or more input beams, the one or more input beams all being produced within a lasing cavity and said frequency conversion member being located within said lasing cavity.

The above said frequency conversion member has frequency conversion means are hereinbefore described with reference to the optical modulation region. Preferably, the frequency conversion member is configured to emit a beam with a frequency substantially equal to the difference in frequency between two input beams. More preferably, the frequency conversion member is configured to emit radiation in the THz frequency range (i.e. 100 GHz to 20 THz).

The lasing cavity may be the lasing cavity of a pulse laser. It may also be the lasing cavity of one or more CW laser sources, e.g. solid state diodes.

The second aspect of the present invention is particularly of use in the field of difference frequency generation, e.g where two beams at visible frequencies $\omega_{vis1}$ and $\omega_{vis2}$ are converted to THz radiation at $\omega_{THz}$ via non-linear difference frequency generation $\omega_{THz}=\omega_{vis1}-\omega_{vis2}$.

Generating THz radiation using difference frequency generation suffers from the problem that in order to produce THz radiation with a commercially useful power level, either a large power density of input radiation is required or the THz signal must be amplified.

The conversion efficiency ρ from $\omega_{vis1}$ and $\omega_{vis2}$ to $\omega_{THz}$ is given by:

$$\rho = \frac{P(\omega_{THz})}{P(\omega_{vis})} \approx 2\left(\frac{\mu}{\varepsilon_0}\right)^{\frac{3}{2}} \frac{\omega_{vis}^2 d^2 l^2 \sin^2\left(\Delta k \frac{l}{2}\right)}{\left(\eta^3\left(\Delta k \frac{l}{2}\right)\right)^2} \frac{P(\omega_{vis})}{A}$$

Where A=area of the beam, d=second order non-linear optical coefficient, η is the refractive index at $\omega_{vis}$, l is the length of the non-linear crystal, and where $\omega_{vis}=\omega_{vis1}\approx\omega_{vis2}$ $\Delta k = k(\omega_{vis2}) - k(\omega_{vis1}) - k(\omega_{THz})$ (expresses momentum conservation).

It is difficult and expensive to provide an input beam at $\omega_{vis}$ with a very high power density outside of a conventional laser cavity. Using amplifiers to amplify either the input radiation or the emitted THz signal increases the bulkiness and the cost of the source. It is precisely this increased size and cost which currently limits the proliferation of THz imaging systems in potential commercial applications.

In the present invention, the frequency conversion member is actually placed within the laser cavity of the input beam or beans, and thus it is termed an intra-cavity structure, Thus, high powers of the input beam are accessed inside the laser cavity, resulting in larger THz powers, without having to resort to bulky or expensive amplifiers placed external to the cavity to realise high input beam powers.

In the following description, the input beam or beams will be referred to as having a frequency of $\omega_{vis1}$, $\omega_{vis2}$ etc., or more generally $\omega_{vis}$ as, in general, $\omega_{vis1}\approx\omega_{vis2}$. The emitted beam will be referred to as having a frequency of $\omega_{THz}$. However, it will be appreciated by a person skilled in the art that although it is preferred that a THz signal is emitted, radiation of other wavelengths could be produced using the radiation source of the present invention In particular, radiation could include mid-infrared (20 THz–90 THz), near-infrared (90 THz–300 THz), and millimeter wave/microwave frequencies (100 GHz–10 GHz). A wide bandwidth signal with powerful components at frequencies ranging from the millimeter wave to near-infrared is achievable with this invention, and this would have wide ranging applications in imaging and spectroscopy.

The intensity of the input beam at $\omega_{vis}$ inside a laser cavity exceeds its value outside the lasing cavity by $(1-R)^{-1}$, where R is the lowest reflectivity of the mirrors (at $\omega_{vis}$) within the cavity for the input beam itself If R=1, the intensity enhancement inside the cavity is very large and hence any THz power at $\omega_{THz}$ generated by placing a frequency conversion member inside the cavity is also greatly enhanced.

The apparatus can be configured such that one can extract the total available power of the laser at $\omega_{THz}$ instead of at $\omega_{vis}$ and obtain 100% conversion efficiency However, the frequency conversion member located within the lasing cavity inevitably results in additional losses within the cavity at $\omega_{vis}$. This results in a reduction of the power density ($P(\omega_{vis})$) in the cavity.

One of the mirrors in the input beam (laser) resonator is referred to as an output coupler and reflects a majority of the input beam back into the laser cavity, allowing (with other components) for lasing action in the cavity at $\omega_{vis}$. The reflectivity of the output coupler is changed (increased) to cancel any losses of power at $\omega_{vis}$ inside the resonator which arise when the frequency conversion member is inserted. If no input beam power at $\omega_{vis}$ is required, the reflectivity R of the output coupler is ideally set to 100% so that all the power at $\omega_{vis}$ remains in the cavity and contributes to the THz generation from the frequency conversion member. However, many practical imaging and spectroscopy systems will require output from the system at both $\omega_{vis}$ as well as $\omega_{THz}$, and in this case R is preferably set between 90–100% at $\omega_{vis}$.

The output coupling means may be provided on the opposing side of the frequency conversion member to the side which the input beam or beams first enter the frequency conversion member.

The drop in power occurs at the laser output of $\omega_{vis}$ external to the cavity. This is not of direct concern in making a more powerful THz source.

The output coupler is preferably provided by a member which has substantially zero reflectivity to the emitted radiation and highly reflective to the radiation of the input beam or beams. Preferably, this high reflectivity is between 90% and 100%. Thus, the output coupler allows the THz radiation to exit from the cavity, but confines the input beam radiation to within the optical cavity to generate further THz radiation from the frequency conversion member.

The output coupler can be configured to allow a source according to the present invention to emit both THz radiation and input beam radiation. (The advantages of this will be described with reference to imaging systems later in this description.)

Preferably, the output coupler is arranged so that the THz radiation is emitted from the cavity before it is reflected back onto the lasing element which generates the input beam or beams.

To produce THz radiation, the frequency conversion member will preferably be a non linear crystal which is preferably configured to emit a frequency which is substantially equal to the difference of two frequencies provided by the input beam or beams.

The incident radiation generates a time dependent polarisation via the second order non linearity of the material. A simplified view of the mechanism is to picture the electrons in the material as being on springs. The incident radiation causes the electrons to vibrate with frequencies corresponding to the incident frequencies, their sum and their difference. Vibration occurs at sum and difference frequencies due to the non linear nature of the spring vibration.

Which frequency is emitted is dependent on the non-linear coefficients of the material at the fundamental frequency, and phase matching between the non-linear polarisation and generated/converted radiation at the difference frequencies.

The efficiency of the THz generation from two visible photons $\omega_{vis1}$ and $\omega_{vis2}$ is governed by two key material properties, which are summarised below:

1. The Second Order Susceptibility, $\chi^{(2)}$

The magnitude of $\chi^{(2)}$ determines the conversion strength of the visible electric field to THz electric field, and is related to the degree of asymmetry of the electric potential at the microscopic level. This is evident from the fact that the THz power generated is proportional to the polarisation of the material $\rho(\omega_{THz})$ oscillating at $\omega_{THz}$ given by:

$$\rho(\omega_{THz}) \chi^{(2)} E_{vis1} E_{vis2}$$

Crystals which have a large $\chi^{(2)}$ which are suitable for the frequency conversion member are:

$LiIO_3$, $NH_4H_2PO_4$, ADP, $KH_2PO_4$, $KH_2AsO_4$, Quartz, $AlPO_4$, ZnO, CdS, GaP, GaAs, $BaTiO_3$, $LiTaO_3$, $LiNbO_3+$, Te, Se, ZnTe, ZnSe, $Ba_2NaNb_5O_{15}$, $AgAsS_3$, proustitie, CdSe, $CdGeAs_2$, $AgGaSe_2$, $AgSbS_3$, ZnS, BBO, KTP and organic crystals such as DAST (4-N-methylstilbazolium).

2. The Refractive Indices for the Visible and THz Fields ($\eta_{vis}$ and $\eta_{THz}$)

These govern the degree of phase matching between the optically induced non-linear polarisation and the generated THz, which need to interfere constructively throughout the crystal. Materials with a large difference between $\eta_{vis}$ and $\eta_{THz}$ suffer from poor conversion efficiencies. Phase matching ensures that the momentum k is conserved between the visible photons with momentum at or near $k(\omega_{vis})$, and the THz photons with momentum $k(\omega_{THz})$ which are generated by the frequency conversion member. Phase matching for generating THz radiation from the difference frequencies of the incident radiation is expressed as:

$$\Delta k = k(\omega_{vis} + \omega_{THz}) - k(\omega_{vis}) - k(\omega_{THz}) \approx 0.$$

The coherence length, $l_c$, which is a measure of the distance over which the optically-induced non-linear polarisation and the generated THz electric fields remain in phase, is defined:

$$l_c = \pi c / (\omega_{THz} |\eta_{vis} - \eta_{THz}|)$$

where $\eta_{vis}$ is the refractive index of the material at visible frequencies and $\eta_{THz}$ is the refractive index of the material at THz frequencies.

Thus, for the long coherence length necessary for efficient THz generation, $\eta_{vis} - \eta_{THz}$ must be small. However, inorganic non-linear optical materials have a large index mismatch and so $l_c$ may be no larger than a few microns.

Therefore, it is preferable if the frequency conversion means of the second aspect of the invention also comprise phase matching means for enhancing the phase matching between at least two different frequency signals propagating in the frequency conversion member in response to illumination by the one or more input beams, the phase matching means having a spatial variation in its refractive index along a component of the input radiation beams.

Some materials have a natural degree of phase matching due to birefringence properties. In this case, phase matching can be achieved over at least a certain length of the material. However, many materials with large optical non-linearities nevertheless suffer from having no birefringence or other properties which allow some degree of phase matching and thus the full realisation of the material as frequency converter.

Preferably, the phase matching means are provided in the frequency conversion member to reduce this variation in the refractive indices at the different frequencies.

Alternatively, or in addition to the spatial variation in the refractive index, the phase matching means may be provided for by a periodic modulation in the frequency converting non-linear coefficient along the axis of the input beam or beams.

Preferably, there will be a single input beam which provides two frequency components. This can be achieved by a pulsed laser. Preferably, the pulsed laser will have a pulse width ranging from 10 fs to 10 ps.

Losses due to the frequency conversion member can be reduced if the frequency conversion member is cut at the Brewster's angle for the polarisation and frequency of the input radiation. Alternatively, the frequency conversion member could be anti-reflection coated to reduce losses at $\omega_{vis}$. Preferably, the frequency conversion member is also a material which has minimum absorption at $\omega_{THz}$ due to mechanisms such as phonon absorption etc.

Preferably the two different frequency components are provided by a pulsed laser source. A pulse laser source is desirable because mode matching and beam overlap between the input beams are required to obtain optimum conversion to THz. This problem is circumvented if a single beam provides both frequency components ($\omega_{vis1}$ and $\omega_{vis2}$) Also, the higher fields obtainable by pulsed lasers allow the (progressively smaller) non linearities in the polarisation term to be accessed and the radiation pulse produced by a pulsed laser inherently contains a number of different frequencies making it ideal for difference frequency generation over a broad range.

The radiation source of the second aspect for the present invention is particularly useful in a THz imaging system. Previous THz imaging systems have been bulky because amplifiers external to the laser cavity are required to produce sufficiently large THz powers for applications. Such external amplifiers are bulky, very expensive, and very difficult to operate. Moreover, the addition of such an amplifier results in a reduction of the pulse repetition rate, which lowers the signal to noise ratio associated with the THz image and its quality. These aspects have made the widespread use of THz imaging prohibitive in terms of size, cost, ease of use, quality of images, and image acquisition times. Therefore, an imaging system which uses the source of the second aspect of the present invention provides considerable advantages in that the system is a) more compact, b) less expensive, c) more user-friendly and d) may provide better signal to noise ratios due to the higher pulse repetition rate and higher THz power levels, and e) may provide faster data acquisition times, allowing for collection of THZ images at video frame rates.

Therefore, in a third aspect, the present invention provides an imaging system comprising a radiation source and a detector, the radiation source comprises a frequency conversion member for emitting a beam of radiation in response to a radiation by one or more input beams, the input beam having a frequency different to that of the one or more input beams, the one or more input beam or beams being produced within a lasing cavity and said frequency conversion member being located within said lasing cavity.

It will be appreciated that the radiation source can be configured as described with reference to the first aspect of the present invention. The imaging system basically comprises three main sections, a generation section for generating the imaging radiation (including the THz beam and visible detection beam), an imaging section for imaging a sample and a detection section for detecting the radiation once it has passed through the imaging section. The generation section will be provided by a source in accordance with a first aspect of the present invention.

Preferably, wherever possible mirrors will be used instead of transmission optics to minimise losses associated with transmission optics, i e.
 (i) frequency dependent refraction losses and amplitude pattern distortion at dielectric (e.g. air-lens) interfaces
 (ii) frequency dependent absorption losses
 (iii) diffraction effects and distortions of the field distributions due to power falling on the lens surface at an angle.

Preferably, the THz radiation is directed onto the sample by means of a off axis parabolic (OAP) mirror. In such a mirror, there is a constant phase difference between the incident and reflected beam across the surface of the mirror.

More preferably, an even number of OAP mirrors are used and each adjacent pair are separated by the sum of their focal lengths. In this configuration, the size of the beam waist (minimum beam diameter normal to the beam axis), after reflection from the second mirror in the sequence, is frequency independent. This is also true for the last optical element in a chain providing that there are an even number of optical elements in the chain.

This configuration is particularly advantageous for THz imaging because a THz pulse is made up from a large number of frequency components and it is required to keep the size of the imaging beam constant for all THz frequencies in the pulse. Similar considerations apply for directing the THz radiation, collected from the object which is the subject of the imaging, towards the detection section.

Alternatively or in addition to OAP mirrors, condenser cones may also be used, which may be made of brass or copper, highly polished on the inside and with electroplating and/or gold/silver evaporated coating. These are preferably located next to the sample which is to be imaged. More preferably within a few wavelength of the sample i.e. 50 $\mu$m to 100 $\mu$m. The cones preferably have an entrance aperture of diameter about 2 mm and an exit aperture of between 50 $\mu$m to 100 $\mu$m.

Lenses may also be added, preferably these are chosen from non dispersive materials such as high density polyethylene (EDPE), polytetrafluorethylene (PTFE) and high resistivity Silicon. The materials are preferably non dipersive to avoid temporal broadening of the THz pulse.

Preferably, the imaging system of the third aspect comprises a motorised stage for supporting a sample which is to be imaged. The stage is preferably moveable in two directions orthogonal to the beam axis.

Preferably, the detector used in the imaging system of the third aspect is a non linear crystal and is preferably configured to detect THz radiation using the AC Pockets effect. Here, the detector is configured to rotate the polarisation vector of a first input beam in response to illumination with a THz beam and emit a beam with the polarisation vector rotated.

The first input beam can be thought of as a reference beam, the second beam is the detected beam. Before entering the detector, the polarisation of the reference beam and the detected beam are rotated such that they are parallel to one another and have a component along both the ordinary and extraordinary axes of the modulation region.

The reference beam and the detected beam are preferably linearly polarised before entering the detector. However, one or both of them may also be circularly polarised.

The detector is configured so that the detected beam (if present) rotates the polarisation of the reference beam by an angle. If the detected beam is not present, the reference beam may become slightly elliptically polarised during its passage through the detector crystal. To compensate for this effect, the beam emitted from the detector crystal is preferably passed through an optical correction circuit.

Preferably, the optical correction circuit converts the linearly (or elliptically) polarised beam into a circularly polarised beam.

The emitted linearly (or elliptically) polarised beam is preferably converted into a circularly polarised beam by a variable retardation waveplate e.g. a quarter waveplate. Preferably, this circularly polarised beam is then passed into a polarisation splitting device (such as a Wollaston prism) which separates the circularly polarised radiation into two linear components. If the detected beam is not present, these linear components are equal: If the detected beam is present, these linear components are not equal to one another.

Preferably, the two output beams from the prism are incident on a balanced photodiode assembly, which produces a non-zero output signal if there is a difference in magnitude between the two beams.

Alternatively, the reference beam can be circularly polarised before entering the detector. This can be achieved by putting the variable retardation waveplate in the path of the reference beam before it reaches the detector, and replacing the variable retardation waveplate after the detector with for example, a half waveplate if the variable retardation waveplate is a quater waveplate. The detected beam (if present) changes the circularly polarised reference beam into an elliptically polarised beam. The elliptically polarised beam is then separated into its two components by a Wollaston prism or the like as described previously.

A variation on the prism and balanced photodiode configuration uses two crossed polarizers situated on either side of the detector. The reference beam is passed through the first polarizer, and transmitted through the detection crystal along with the THz beam. If the THz beam is present, the polarisation of the reference beam will be rotated such that the beam has a component in a transmission direction of the second polarizer. If the THz beam is not present, the polarisation of the reference beam is not rotated and hence is blocked by the second polarizer.

The reference beam is preferably produced by the generation section. The radiation carrying the image information is then detected by the detector using the reference beam. Preferably, a control system is provided which provides a time variation between the input beam and the reference beam. The control system may be inserted into either the generation or the reference beam paths.

The control system may comprise a motorised mirror which can be oscillated backwards and forwards along the beam axis in order to increase or decrease the optical path length of the reference beam.

The system may also comprise optics to enlarge the cross sectional area of the reference beam before it enters the detection system. Preferably, the cross sectional area of the reference beam will be larger than that of the imaging radiation, to ensure that the whole of the imaging beam cross-section is detected. The detection section may also comprise a CCD camera with a detection area which is larger or the same size than the area of the reference beam. Thus, the CCD camera reads a 2D image and there is no need to move the sample during imaging.

Alternatively, the control system may comprise a grating pair configured to extend the pulse width of the reference beam. An optical fibre cable can also be configured to extend the pulse width of the reference beam. These cause the different wavelength components of the pulsed reference beam to travel through the detector crystal at very different times.

The detection section may comprises a grating spectrometer, to disperse the wavelengths. The detection section may also comprise a CCD camera to record the spatial distribution from the spectrometer.

Possible materials which posses good non-linear characteristics for either difference frequency generation or detection are GaAs or Si based semiconductors. More preferably, a crystalline structure is used. The following are further examples of possible materials:
$NH_4H_2PO_4$, ADP, $KH_2PO_4$, $KH_2ASO_4$, Quartz, $AlPO_4$, ZnO CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_2$, ZnS, organic crystals such as DAST (4-N-methylstilbazolium).

In general, non-centrosymmetric crystals are used for second order effects. Third order effects are found in a variety of different crystals with varying strengths.

BRIEF DESCRIPTION OF THE DRAWINGS

The present invention will now be described by way of example and with reference to the following non-limiting embodiments in which:

FIG. 19 shows a calculation of the band structure of a triangular lattice of holes in GaAs for a "bulk" case;

FIG. 20 shows another calculation of the band structure where a wave guide with a finite thickness is modelled;

FIG. 21 shows a further band structure calculation for a wave guide with a finite thickness;

DETAILED DESCRIPTION OF THE INVENTION

FIG. 1 shows schematically four generation processes which will benefit from the phase matching of the present invention.

Figure 1A:
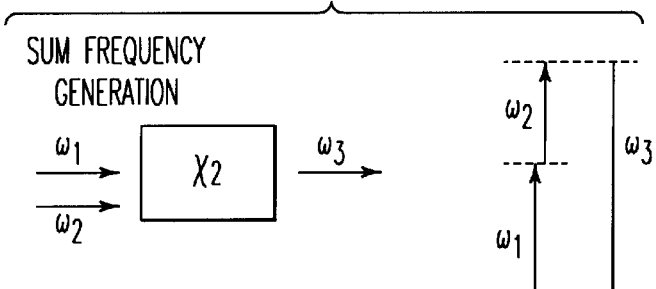
FIG. 1 is a schematic showing sum frequency generation, difference frequency generation, second harmonic generation and optical parametric generation.

FIG. 1a shows sum frequency generation. Two input frequencies $\omega_1$ and $\omega_2$ are incident on a material with a large second order susceptibility ($\chi_2$) such that the $\omega_1$ and $\omega_2$ are together to generate frequency $\omega_3$, where $\omega_3$ equals $\omega_1 + \omega_2$.

Figure 1B:
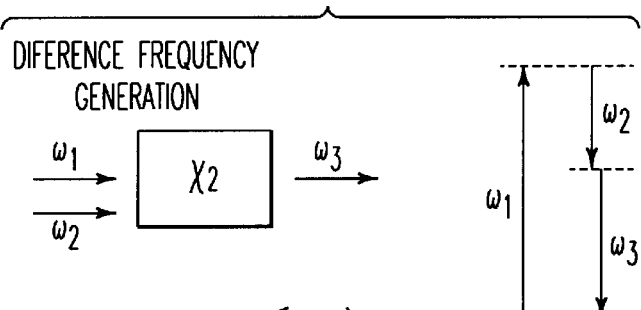

FIG. 1b shows schematically difference frequency generation. Here, incident frequencies $\omega_1$ and $\omega_2$ subtract to generate frequency $\omega_3$. Emitted frequency $\omega_3$ equals $\omega_1 - \omega_2$.

Figure 1C:
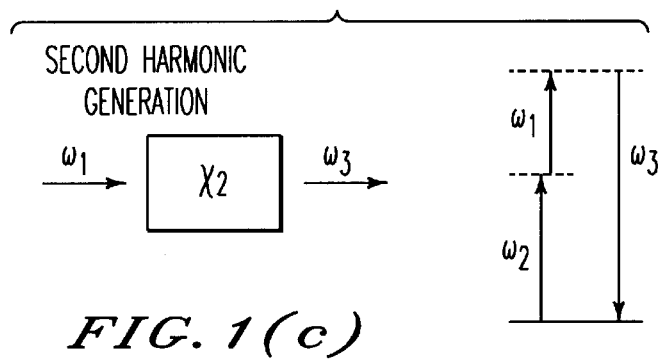

FIG. 1c shows second harmonic generation, Here, there is one input frequency $\omega_1$ and the generated frequency is twice $\omega_1$. In other words, $\omega_2$ equals $\omega_1 + \omega_1$.

Figure 1D:
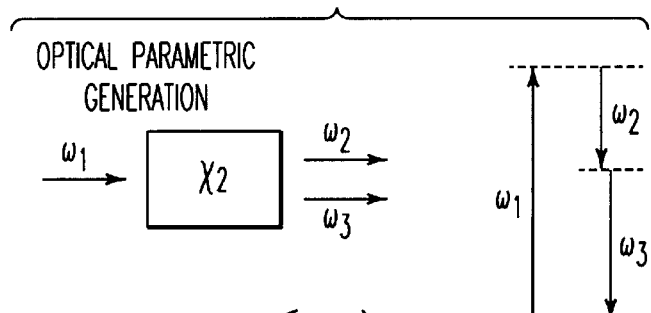

FIG. 1d shows optical parametric generation where a single input frequency $\omega_1$ generates two output frequencies $\omega_2$ and $\omega_3$. $\omega_1$ equals $\omega_2 + \omega_3$.

Figure 2:
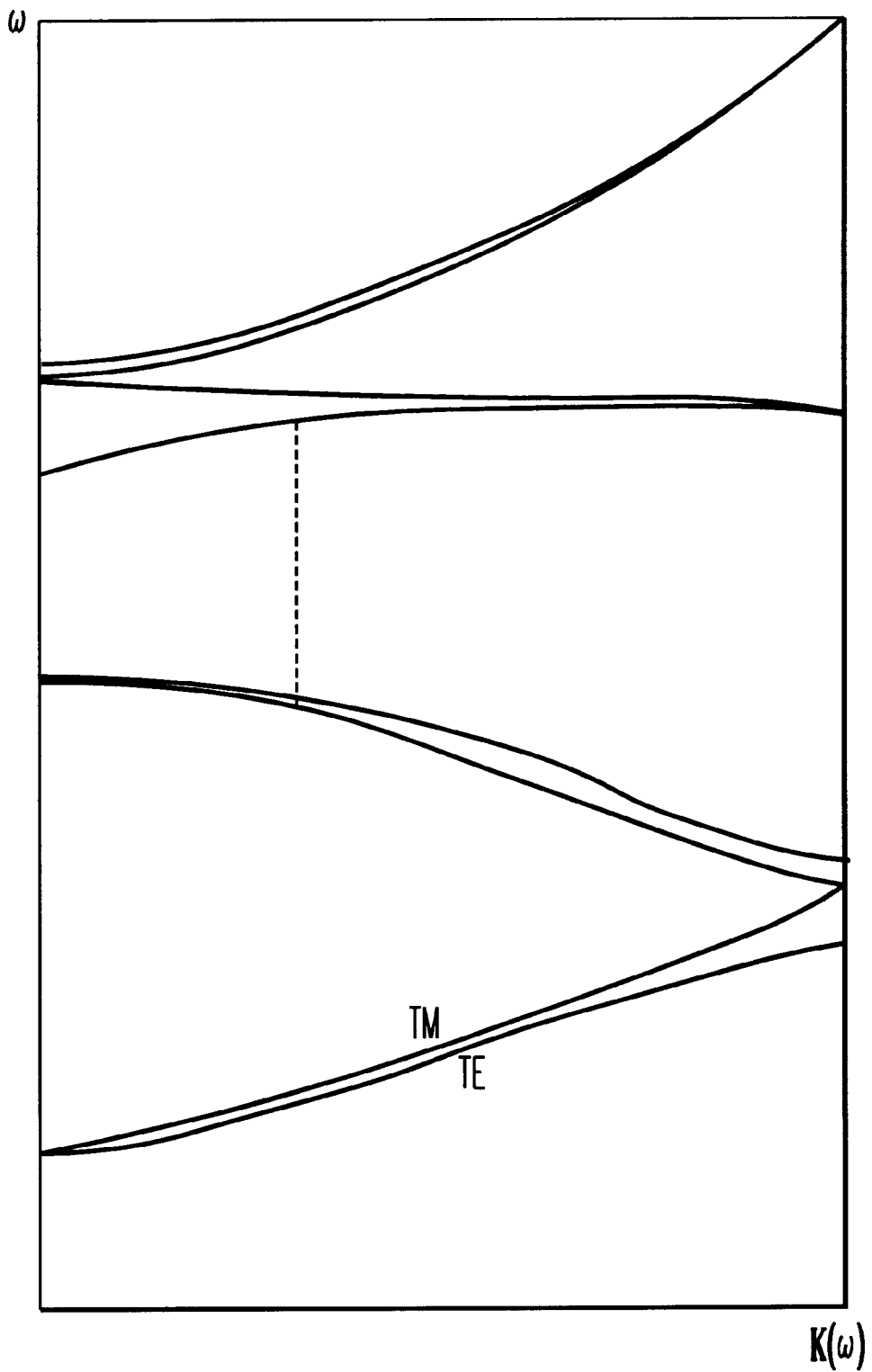
FIG. 2 schematic dispersion modes for visible photons in a structure in accordance with an embodiment of the present invention.

In FIG. 2, the solid lines are calculated dispersion curves ($\omega$vs. k) for optical phonons in a waveguide structure with a GaAs core and $Al_{0.33}Ga_{0.67}As$ cladding layers plotted as a function of in-plane wave vector. The lattice periodicity introduces a zone boundary at which the dispersion curves are folded back. This permits the phase matching condition to be satisfied for a pair of optical modes if the corresponding points on the diagram are connected by a line with a gradient equal to that of the emitted radiation (in this case THz) light line, This construction indicates which combination of modes are dynamically allowed. The strength of the emitted THz radiation is governed by the transition matrix between the initial and the final states, which, in turn, depend on the degree of mixing introduced by the photonic band-gap. The stronger the modulation, the greater the efficiency of THz emission.

The dotted lines show other possible modes which can be used to excite THz radiation. Different optical modes can be excited by illuminating the structure at different angles of incidence to the match the in-plane wave vector or by coupling directly at the cleaved edge.

It should be understood that although the invention will be described using visible light dispersion curves, the inverse can also be envisaged where the folding back of THz dispersion curves at the zone boundary to allow the phase matching condition to be satisfied.

Figure 3:
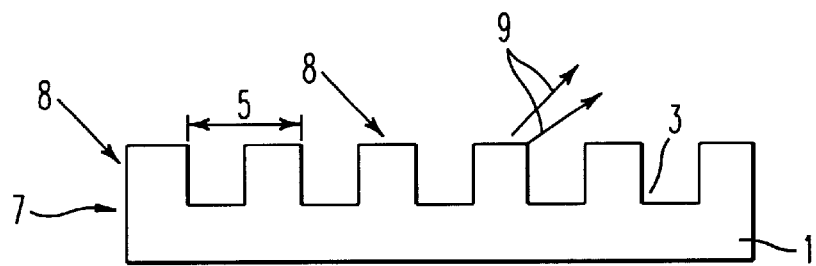
FIG. 3 is a schematic of a structure in accordance with an embodiment of the present invention.

FIG. 3 shows a simple structure which achieves phase matching of the present invention. A GaAs wafer 1 is etched to form etch pits 3. The etch pits are left unfilled. Air has a lower refractive index than GaAs at both visible frequencies and THz frequencies.

The pitch of the structure 5 is 1.5 $\mu$m and the pits are etched to a depth of 1 $\mu$m and have a width of 1 $\mu$m.

Radiation is incident from side 7. This will allow emission of THz or blue radiation 9 depending on the exact configuration of the structure. The radiation may also be incident at an angle to the structure 8 and also enters either at the edge of the sample or through the top surface. This also applies to the structures shown in FIGS. 4 to 11 and 14 to 18. Phase matching occur if there is a component of the momentum wave vector k, parallel to the direction of variation of the refractive index.

The laser radiation source is a Ti:Sapphire laser which typically produces wavelengths in the range of 900 nm to 350 nm, with a pulse width of 50 fs and a repetition rate of 82 MHz. Other types of lasers may be used, for example, pulsed lasers such as erbium doped fibre lasers or semiconductor pulsed lasers may be used. Two CW semiconductor diode lasers operating at slightly different frequencies can also be used.

In general, any crystal can be used which is non-centrosymmetric to excite second order frequencies. For example, the following can be used:

$LiIO_3$, $NH_4H_2PO_4$, ADP, $KH_2PO_4$, $KH_2ASO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium).

Figure 4:
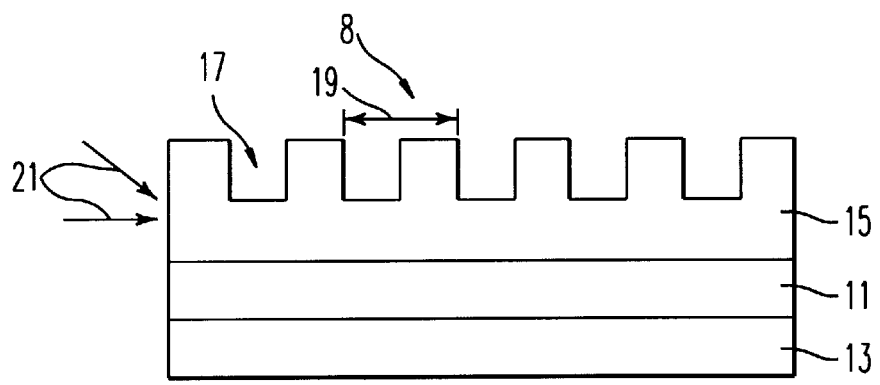
FIG. 4 shows a similar structure to FIG. 3 with cladding layers.

FIG. 4 shows a structure similar to FIG. 3 except with cladding layers. An $Al_{0.33}Ga_{0.67}As$ cladding layer 11 is formed on an upper surface of a GaAs substrate 13. 400 nm of GaAs 15 are formed on cladding layer 11. 200 nm deep etch pits 17 are then etched into the GaAs layer 15. Again the pitch of the structure 19 is 1.5 $\mu$m. The incident radiation 21 is optically confined by the cladding layer 11.

Figure 5:
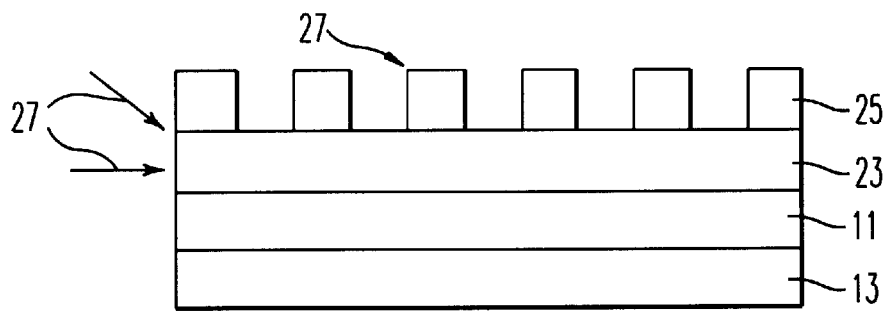
FIG. 5 shows a structure similar to FIG. 3, with cladding layers.

FIG. 5 shows a similar structure to FIG. 4 with a GaAs substrate 13 and $Al_{0.33}Ga_{0.67}As$ cladding layer 11. Here, a GaAs layer 23 is formed and a $Al_{0.33}Ga_{0.67}As$ cap cladding layer 25 is formed on an upper surface of the GaAs layer 23. This layer is then etched completely away in parts to form a series of islands of AlGaAs.

Incident radiation 27 is mainly confined to the GaAs core layer 23. However, a small but significant portion of the field is also in the AlGaAs cap cladding layer 25. Thus, the variation in the refractive index of AlGaAs cap cladding layer 25 affects the momentum of the visible photons and thus enhances the phase matching.

Figure 6:
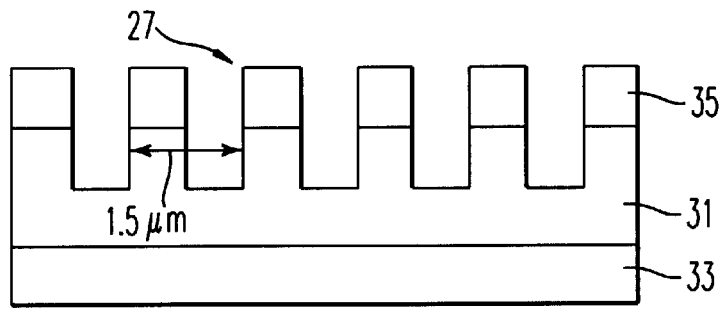
FIG. 6 shows a structure similar to FIG. 3 with cladding layers.

In FIG. 6, $Al_{0.33}Ga_{0.67}As$ layer 31 is formed on an upper surface GaAs substrate 33. A layer of $Al_{0.12}Ga_{0.88}As$ cladding layer 35 is formed on an upper surface of layer 31. Etch pits with a 1 $\mu$m width are etched through the layer 35 and partially through layer 31. The pitch of the structure is again 1.5 μm and the total depth of the etch pits are 1.4 μm, The width of the upper layer 25 is 0.4 μm.

The etch pits can be formed by wet etching, reactive ion etching etc. Ideally, the etch walls are substantially perpendicular to the plane of the structure as this allows greater contrast in the refractive index and hence has better phase matching properties than structures with shallow sloping sidewalls.

Figure 7:
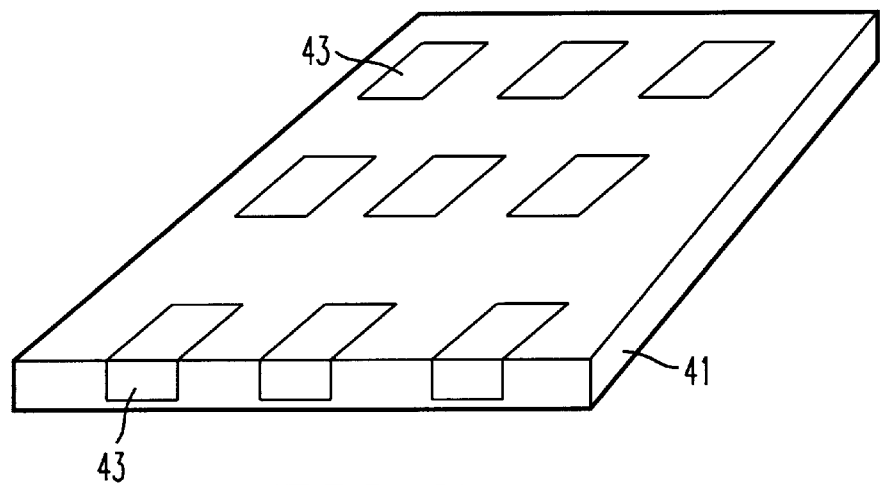
FIG. 7 shows a two dimensional optical structure.

FIG. 7 shows a structure with a variation in the refractive index in two directions. A GaAs substrate 41 is etched with a series of holes 43 to form a 2D array, The holes are 1 μm deep and have a width of 1 μm. The unfilled holes have a lower refractive index than the GaAs 41. Of course, this 2D structure can be used with the waveguides shown in FIGS. 4 to 6.

Figure 8:
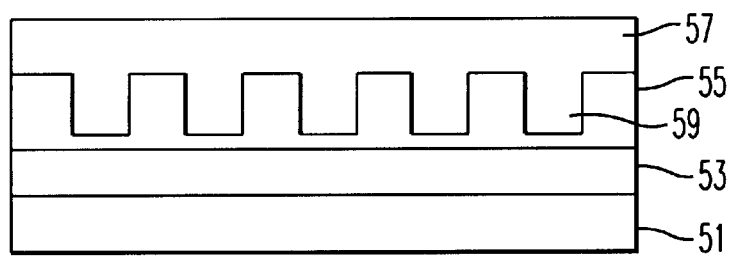
FIG. 8 shows an embodiment of the present invention which may be fabricated using regrowth.

FIG. 8 shows a cross section of a structure using two materials to effect the change in the refractive index. Layer A, 53, is formed on an upper surface of a GaAs substrate 51. Layer B, 55, is formed on an upper surface of layer A, 53. Layer B is etched by wet etching, reactive ion beam etching etc to form etch pits 59 with a depth of 0.4 μm. Layer C, 57 is then regrown over etched layer B. Layer C, 57 fills holes 59 as it is formed.

There are many layer combination possible for layers A, B and C. For example:

A: AlAs AlSb GaSb $Al_xGa_{1-x}As$ InP InP Si (or SiGe)
B: GaAs InAs InAs $Al_xGa_{1-x}As$ InGaAs AlInAs GaAs
C: AlAs AlSb GaSb $Al_xGa_{1-x}As$ InP InP Si (or SiGe)

typically, x can be, for example, 0.33 or lower.

Figure 9:
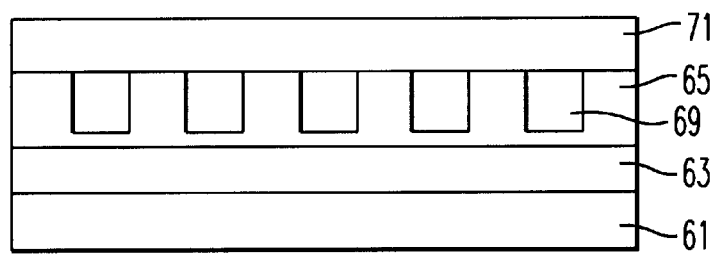
FIG. 9 shows an embodiment of the present invention which may be fabricated using ion beam implantation.

FIG. 9, shows a structure which can be fabricated by ion beam implantation. Layer A 63 is formed on a GaAs substrate 61. Layer B, 65, is formed overlying layer A, 63. Layer B, 65 is then implanted with ions (for example Ga+ ions) in areas 69. Implanting with ions affects the band-gap locally and hence effects a change in the refractive index.

Layer C, 71 is formed on top of layer B, 65. Possible layer configuration for layers A, B and C are given for FIG. 8.

Figure 10:
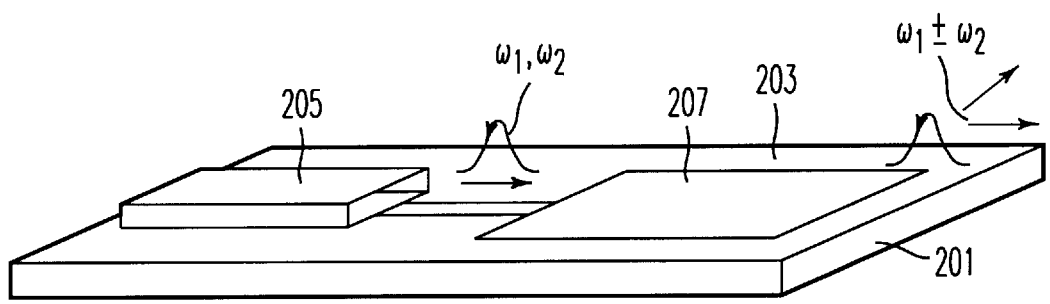
FIG. 10 shows an embodiment of the present invention which may be fabricated with a single laser source.

The structures of FIGS. 8 and 9 also be extended to the 2D modulation structures of the type shown in FIG. 7, FIG. 10 shows an integrated device formed on a substrate 201. A light source which is a semiconductor pulsed laser 205 is formed on an upper surface 203 of the substrate 20. The laser emits a pulsed beam with frequency components $\omega_1$ and $\omega_2$. This beam is inputted into the frequency converter 207 which is provided with frequency conversion and phase matching means such a those shown in FIGS. 3 to 9.

The emitted radiation from the frequency converter 207 is emitted with a frequency of $\omega_1 \pm \omega_2$.

Figure 11:
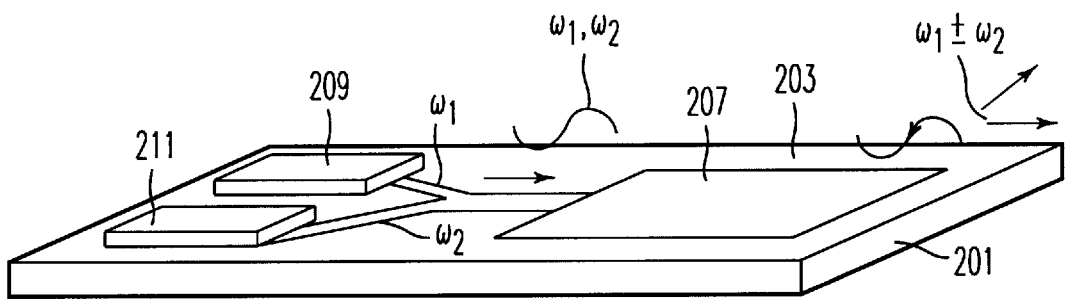
FIG. 11 shows an embodiment of the present invention which may be fabricated with two laser sources.

FIG. 11 shows a similar arrangement to FIG. 10 except here, the input frequencies are provided by two CW lasers, laser 209 (which emits radiation with a frequency of $\omega_1$) and laser 211 (which emits radiation with a frequency of $\omega_2$).

The two frequency components are combined by the frequency converter 207 to emit radiation with a frequency of $\omega_1 \pm \omega_2$ as described in relation to FIG. 10.

Figure 12:
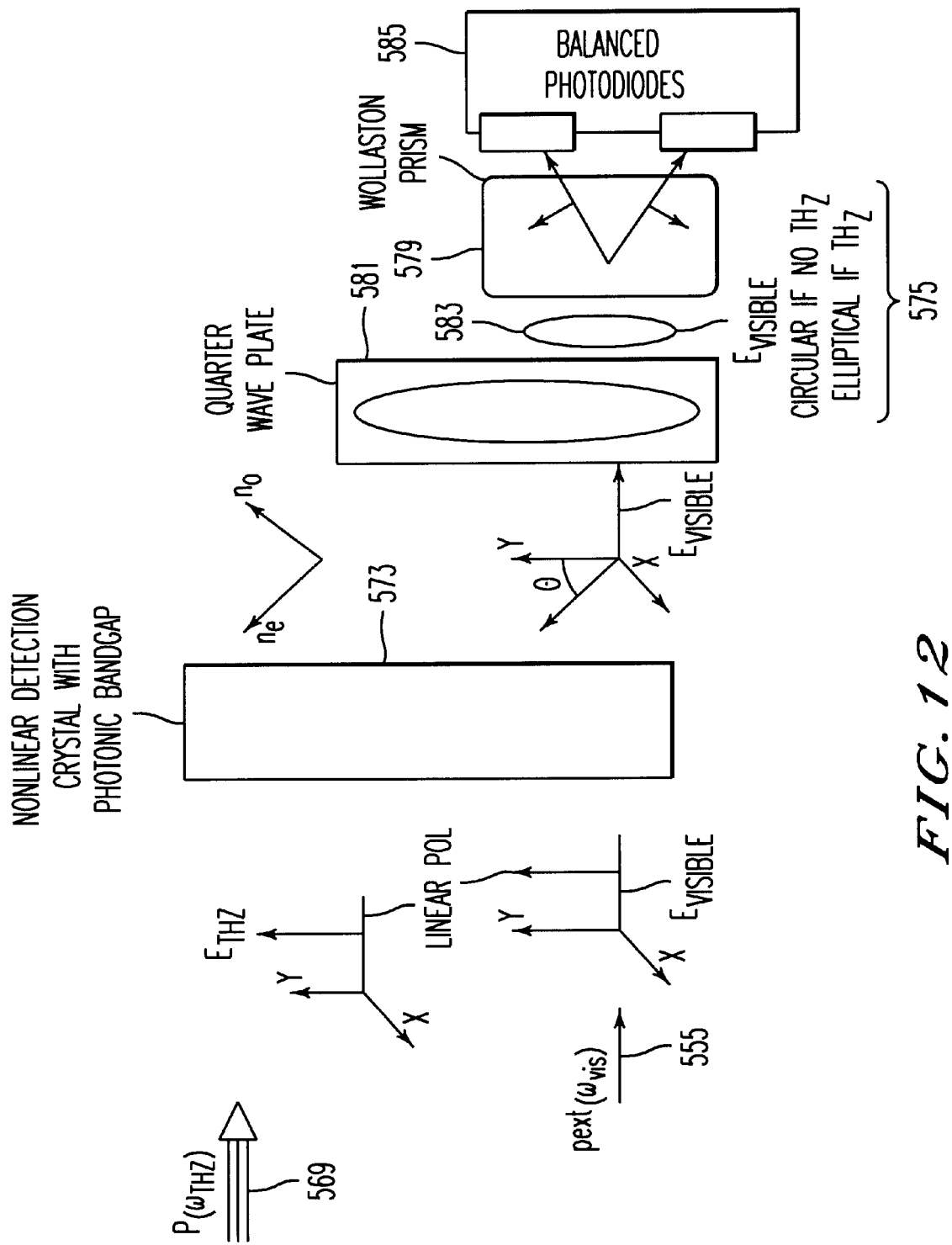
FIG. 12 shows a detection system using an optical device according to an embodiment of the present invention.

FIG. 12 shows a detection system which uses a detection component which requires phase matching of two input frequencies. The detection system uses a AC Pockels effect and is particularly useful for the detection of THz radiation.

A visible light beam 555 which acts a reference beam is incident on detection crystal 573. The reference beam 555 is linearly polarised and the polarisation is oriented such that it has components along both the ordinary and the extraordinary axes of the detection crystal 573. Each of these axes have distinct refractive indices $n_o$ and $n_e$ along the ordinary and extraordinary axes respectively. In the absence of a second radiation beam 569, the linearly polarised reference beam 555 passes though the detection crystal 573 with a negligible change in its polarisation. The applicant wishes to clarify that the angle Θ through which the polarisation is rotated by is negligible. However, the linearly polarised beam can become slightly elliptical. This effect is compensated for by optical circuit 575.

The emitted beam is converted into a circularly polarised beam 583 using quarter wave plate 581. This is then turned back into a two linearly polarised beam by a Wollaston Prism 579 (or equivalent device for separating orthogonal polarisation components) which directs the two different linear components of the polarised beam onto a balanced photodiode 585. The balanced photodiode 585 is balanced such that the difference in outputs between the two diodes is zero.

However, if the detector 573 also detects a secondary beam 569 (in this case a beam with a frequency in the THz range) as well as a reference beam, the angle Θ through which the polarisation is rotated by is not negligible. This is because the THz electric field modifies the refractive index of the visible (fundamental) radiation along one of the axes $n_e$, $n_o$. This results in the visible field after the detector 573 being elliptical and hence the polarisation components separated by the prism 579 are not equal. The difference in the voltage between the output diodes gives a detection voltage. The reference beam 555 and the THz beam 569 should stay in phase as they pass through the crystal. Otherwise the polarisation rotation Θ is obscured. Therefore, the detection crystal 573 has phase matching means of the types described with reference to FIGS. 3 to 9.

Figure 13:
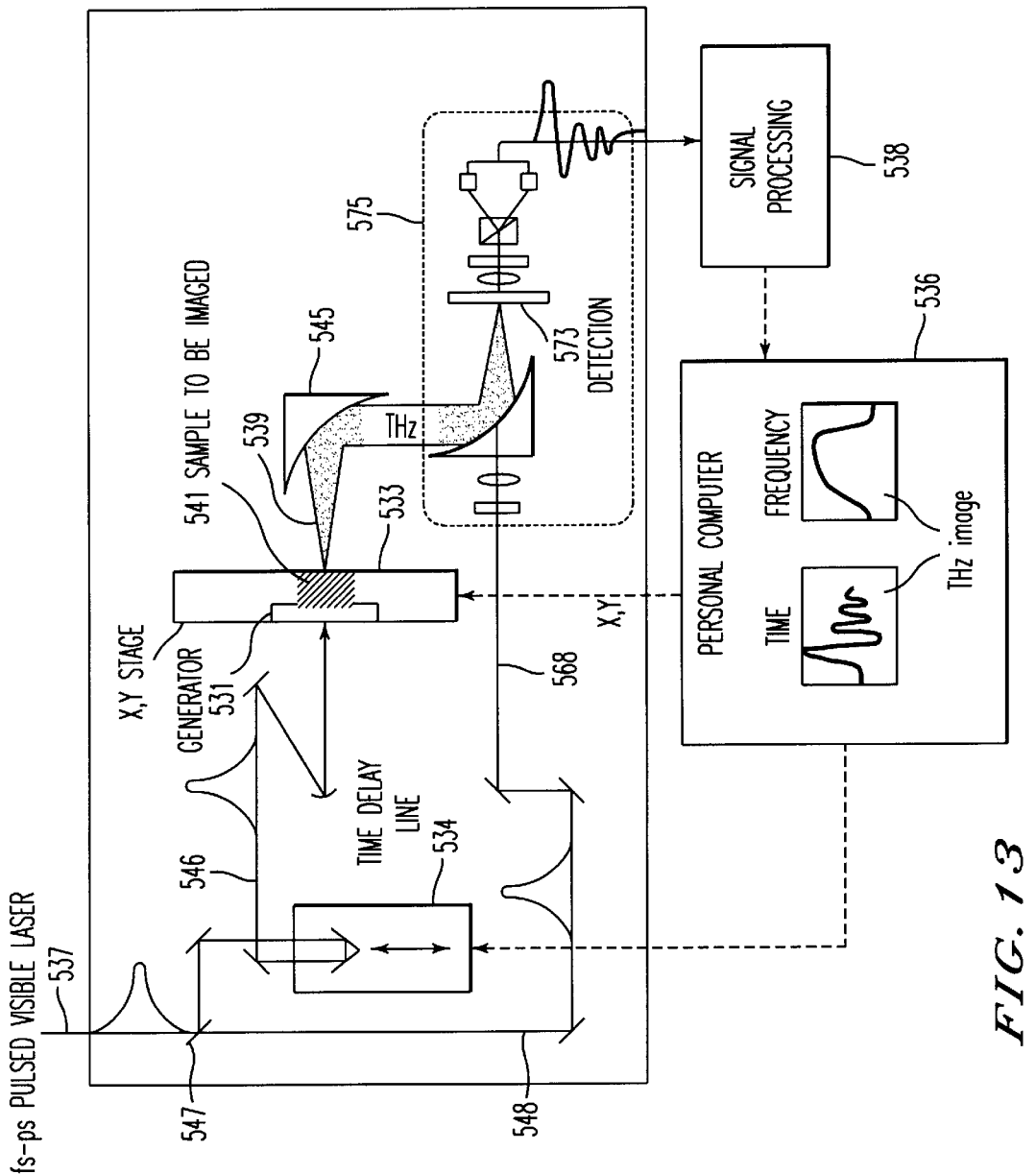
FIG. 13 shows an imaging system using an optical device in accordance with an embodiment of the present invention.

An imaging system particularly suitable for THz application using the frequency conversion system of FIGS. 10 and 11 and the detection system of FIG. 12 is shown in FIG. 13.

The input beam is provided by a pulse laser source 537. The beam is split by a partially reflecting mirror or beam splitter 547 to provide an input beam 546 for generating THz signals and a reference beam 548 for detecting the imaged radiation. The input beam 546 is time delayed by system 534.

The input beam 546 is inputted into frequency conversion generator 531 which is a ZnTe crystal or other material with suitable non-linear coefficients (e.g. $LiIO_3$, $NH_4H_2PO_4$, ADP, $KH_2PO_4$, $KH_2ASO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium) or other generators such as photoconductive switches. The sample which is to be imaged is mounted on an X-Y stage 541 which is mounted on the generator 531. The Imaged THz beam 539 is reflected onto a detector crystal 573 with the reference beam 548.

The beam emitted from the detector crystal 573 is fed into optical circuit 575 (which is identical to the optical circuit 575 of FIG. 12). The output from the optical circuit 575 is fed into signal processing unit 538 which is linked to control means 538 which control, the delay between the input beam 546 and the reference beam 548 and the movement of the stage to image sample 541.

Figure 14:
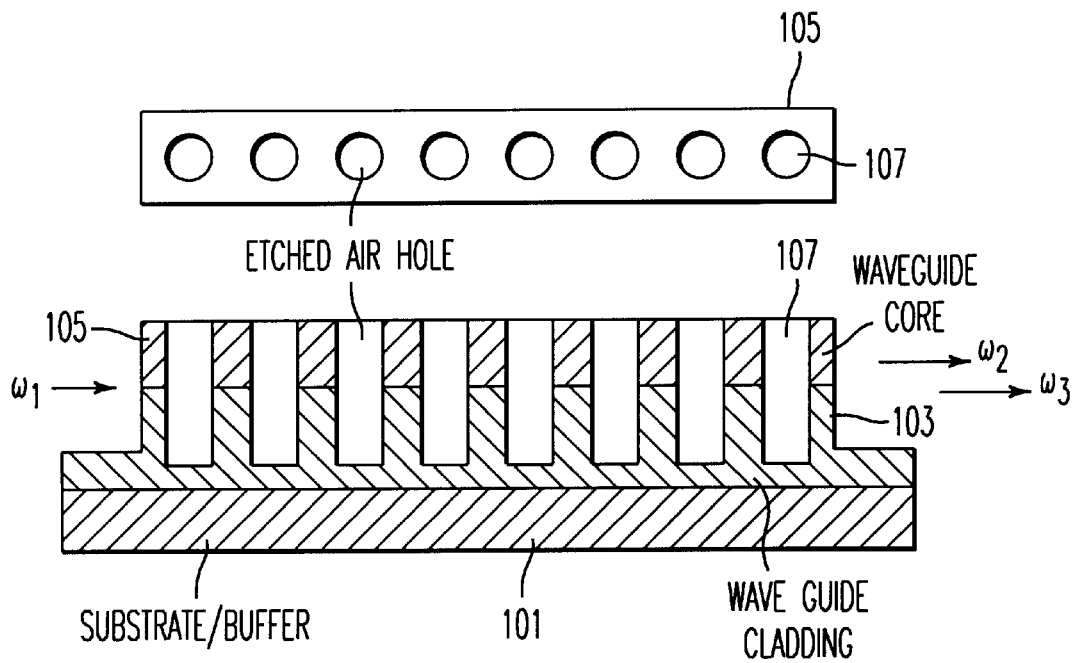
FIG. 14 shows an embodiment of the present invention configured for optical parametric generation, sum generation or harmonic generation.

FIG. 14 illustrates schematically a phased matched material used for optical parametric generation, second harmonic generation or sum frequency generation. A waveguide cladding region 103 is formed overlying a substrate/buffer layer 101. A waveguide core region 105 is formed overlying the waveguide cladding region 103. The waveguide core region 105 is chosen to have a larger effective refractive index than the waveguide cladding region 103, so that an optical mode is confined largely to waveguide core region 105. The waveguide cladding region 103 and the waveguide core region 105 could comprise a single or a multiplicity of layers.

The waveguide core region 105 has a larger refractive index than the waveguide cladding region 103. As an example the waveguide cladding region 103 could comprise $Al_xGa1_{-x}As$ with x=0.3 and the waveguide core region 105 could be GaAs The waveguide cladding region 103 could have a thickness of 0.5–1.0 μm and the waveguide core region 105, 0.2–0.8 μm. As another example, the waveguide cladding layer could compose 1 μm of $SiO_2$ and the waveguide core 0.4 μm of Si. Holes 107 are formed in both the waveguide core 105 and cladding regions 103. These holes could be formed using standard dry or wet etching in conjunction with photolithography or electron beam lithography.

This structure can be optionally topped by another layer of dielectric material (not shown) with a refractive index smaller than that of the waveguide core region after it has been etched.

If FIG. 14 is configured for optical parametric generation, the structure is irradiated with the incident frequency $\omega_1$ leading to the generation of frequencies $\omega_2$ and $\omega_3$, such that $\omega_1=\omega_2+\omega_3$. The holes are formed in the structure so as to modify the dispersion to satisfy the phase matching condition, $\Delta k=k(\omega_1)-k(\omega_2)-k(\omega_3)=0$. The light of frequency $\omega_1$ can be focused onto the waveguide region on the side of the waveguide so that it propagates along the waveguide.

The phase matching condition can also be altered so as to produce efficient second harmonic generation, In this case, a single frequency ($\omega_1$) is incident on the structure, leading to the generation of $\omega_2=2\omega_1$. This is achieved efficiently if the phase matching condition $\Delta k=2k(\omega_1)-k(\omega_2)=0$ is satisfied.

Figure 15:
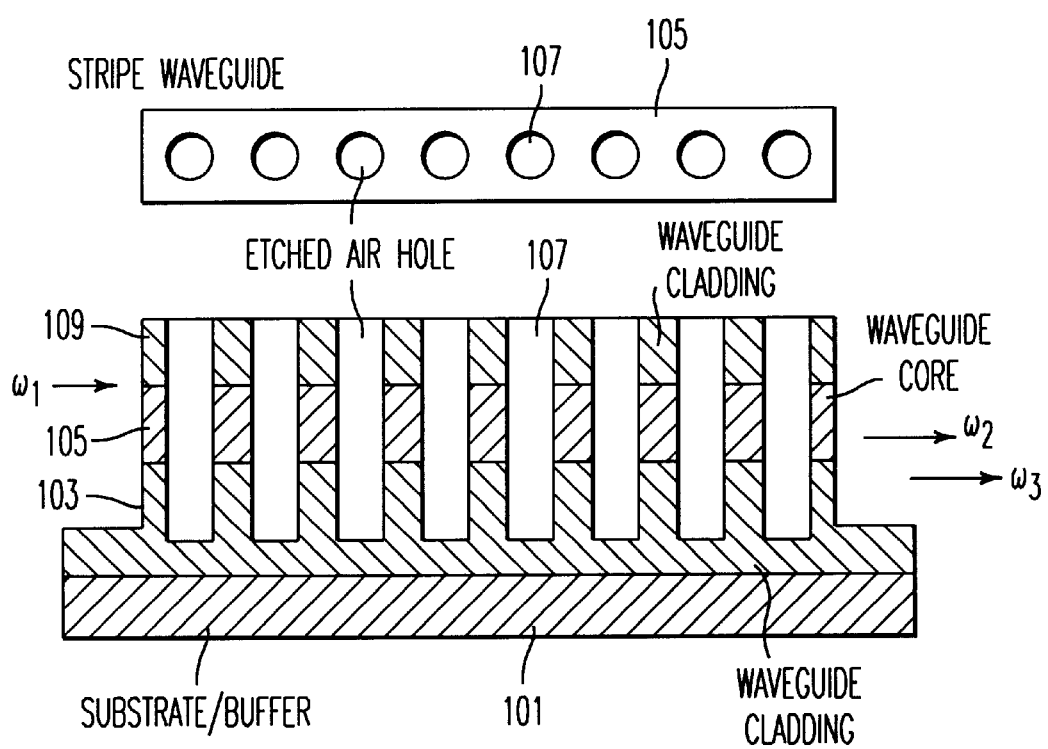
FIG. 15 shows an embodiment of the present invention used for optical parametric generation, sum harmonic generation or harmonic generation.

FIG. 15 shows a similar structure to FIG. 14, where an upper cladding region 109 is provided overlying the core region. This could be a single or multiplicity of layers. It could comprise the same material as the lower cladding layer region 105 or comprise a different material. In any case it should have a smaller refractive index than the waveguide core region 107. This has the advantage of improving the confinement of the optical mode within the core region of the waveguide. As shown here, the holes are etched through the upper cladding region 109, through the core 107 and into the lower cladding region 105. Alternatively the etched holes can terminate in the core region 107 or in the upper cladding region 109.

The non-linear material can be tuned in a number of ways in order to achieve the phase matched condition. For instance the angle or the wavelength of the incident radiation can be changed. Alternatively the temperature of the non-linear medium can be changed.

Figure 16:
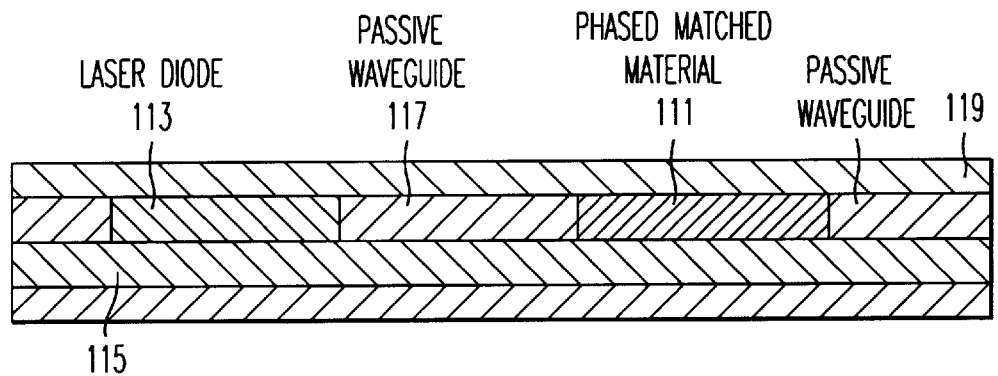
FIG. 16 shows an embodiment of the present invention with a laser source integrated with the optical modulation region.
Figure 17:
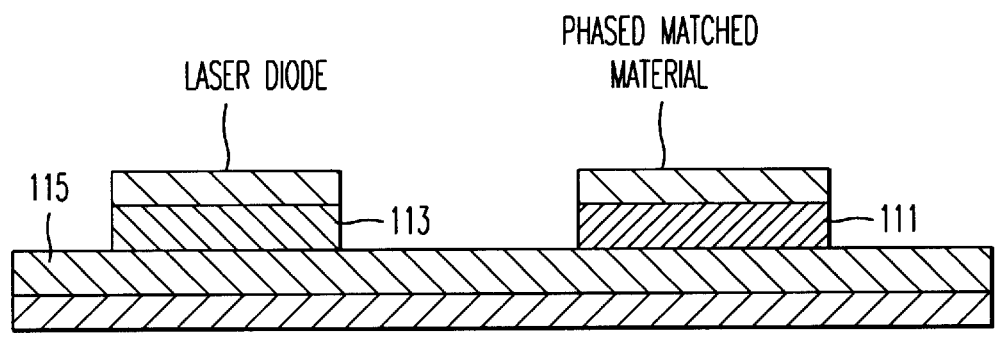
FIG. 17 shows a structure similar to FIG. 16 but with a different waveguide arrangement.

FIGS. 16 and 17 show a phase matching region 111 integrated with an input radiation source 113. The input radiation source 113 can be a conventional CW solid state laser diode. Alternatively, the input radiation source can be a mode-locked solid state laser diode. In a mode locked laser the radiation is concentrated into short pulses and will therefore have the advantage of producing more efficient non-linear frequency conversion in the phased matched material.

In FIG. 16, the light from the laser diode 113 is channelled to the phased matched material 111 by a passive waveguide region 117. It is convenient to arrange the diode laser, which could be a distributed feedback semiconductor laser diode, and the phased matched material within the same waveguide structure. Here the structure is formed on a lower cladding region 115. The active regions of the laser diode and the phase matched materials lie within the core of the waveguide region. The core region is covered by an upper cladding region 119.

FIG. 17 is similar to FIG. 16, except that there is no waveguide between the phased matched material 111 and the laser diode 113. Instead there is an air gap between the two components formed by lithography and etching. For maximum coupling of the output radiation from the laser diode into the phased matched material their separation should be small.

Figure 18:
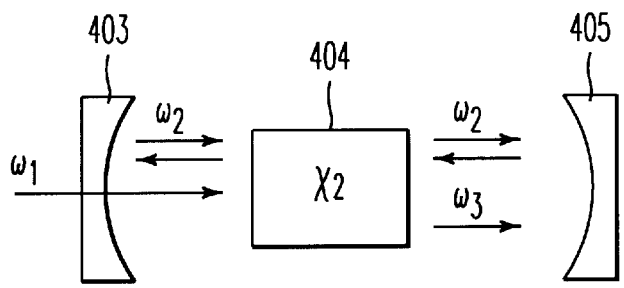
FIG. 18 shows a schematic of an optical parametric oscillator situated within a cavity.

FIG. 18 shows a schematic diagram of an optical parametric oscillator, where mirrors (403, 405) are placed on either side of a non-linear material (401) which is phase matched for optical parametric generation. The mirrors (403, 405) are designed to be highly reflective at frequency $\omega_2$. In this device there is an enhancement of the optical field at frequency $\omega_2$. The mirrors (403, 405) can be fabricated by coating the ends of the non-linear material (401) with a dielectric thin film coating. Alternatively the mirrors (403, 405) can be fabricated using another photonic bandgap material.

FIGS. 19 to 21 show band structure calculations for photonic band gap structures of the type previously discussed. The calculation used to model the band structure shown in FIGS. 19 to 21 is an accurate solution of Maxwell's equation for a patent wave-guide using a semiconductor slab with a lattice of air holes. It has been assumed that there are perfect reflecting mirrors confining the model at the top and bottom of the wave-guide. This is of course, not an exact model of a real wave-guide structure in which the confinement due to guide-cladding interface may be fairly weak.

The calculation follows the method of Cassagne et al. (Phys. Rev. B 53, 7134 (1996) fairly closely, except instead of plane wave basis states TE and TM wave guide modes are used. For a slab of thickness d in the z direction, taking $k=(k_x,k_y)$ as the wave-vector in the in-plane direction $r=(x, y)$, and writing $q=\pi/d$, these modes are $$H_E^k(r, z)=(q^2+k^2)^{-1/2}(q\hat{k}\cos qz-ik\hat{z}\sin qz)\exp(ik.r)$$

$$H_M^k(r, z)=(\hat{k}\times\hat{z}\cos qz)\exp(ik.r)$$

The same results are obtained just using plane waves with an axial component, q, to the wave-vector. The advantage of proper wave guide modes is that they aid in characterising the calculated bands.

With periodic patterning, the field for a wave-vector k in the Brillouin zone can be expressed as a linear combination of these modes with wave-vectors differing by reciprocal lattice vectors G:

$$H(r, z)=\sum_G h_E^G H_E^{k+G}(r, z)+h_M^G H_M^{k+G}(r, z)$$

The wave equation then reduces to a matrix equation $$\sum_G \eta(G-G')\underline{H}_{k+G,k+G'}\begin{pmatrix} h_E^{G'} \\ h_M^{G'} \end{pmatrix} = \frac{w^2}{c^2}\begin{pmatrix} h_E^G \\ h_M^G \end{pmatrix}$$

where $$\underline{H}_{k_1 k_2} = \begin{pmatrix} \sqrt{q^2+k_1^2}\sqrt{q^2+k_2^2}\,\hat{k}_1\cdot\hat{k}_2 & q\sqrt{q^2+k_1^2}(\hat{k}_1\times\hat{k}_2)\cdot\hat{z} \\ -q\sqrt{q^2+k_2^2}(\hat{k}_1\times\hat{k}_2)\hat{z} & k_1 k_2 + q^2 \hat{k}_1\cdot\hat{k}_2 \end{pmatrix}$$

and η (G) is the Fourier transform of the inverse of the dielectric constant ∈(r). For circular holes of radius ρ with internal dielectric constant $\in_a$ in a medium of dielectric constant $\in_b$, $$\eta(G) = \begin{cases} (1-\beta)\varepsilon_b^{-1} + \beta\varepsilon_a^{-1} & (G=0) \\ (\varepsilon_a^{-1}-\varepsilon_b^{-1})2\beta J_1(G\rho)/G\rho & (G\neq 0) \end{cases}$$

Here, β is the fraction of the lattice unit cell occupied by the hole, and $J_1(x)$ a Bessel function.

The matrix equation is solved by a standard numerical diagnoalisation within a basis consisting of a finite set of reciprocal lattice vectors G. The solution is obtained for a series of k along the principal directions in the Brillouin zone.

FIG. 19 shows a band structure for a triangular lattice of holes in GaAs. The lattice constant is 200 nm. The holes are circular holes with a hole radius of 54.6 nm. The filling factor is 0.27. The external index equals 3.5 and the internal index equals 1.0.

The bulk calculation of FIG. 19 is not an ideal model for a wave guide structure, especially close to the cut-off, where the empty waveguide dispersion $$E(k) \alpha \sqrt{(q^2+k^2)}$$

is approximately parabolic, while in the bulk case it is linear, with no cut-off.

The parabolic form of the low energy bands is apparent in FIG. 20, which is the same as FIG. 19 except for the presence of a wave guide of thickness d=400 nm. The differences between the two calculations in the region where the measurements are taken, above 1 eV, are fairly small, with the gaps appearing at roughly the same energies. This is because the lattice constant is smaller than the wave guide width, so q is not very significant compared with the unfolded k values in the measurement region. The difference between empty wave guide and bulk dispersions is small for such large It is believed that if the band gap could be moved to the parabolic part of the empty wave guide dispersion, much larger effects on the band gap are possible. In order to do this, the thickness of the guiding layer has to be reduced, to shift the parabolic region up to an interesting energy, and the lattice constant has to be increased, so that the reciprocal lattice vectors become smaller.

FIG. 21 shows a typical result, for a wave guide of thickness d=130 nm, and lattice constant 1000 nm. The filling factor of 27% is the same as in FIGS. 19 and 20. With this structure there is a complete band gap with a width of about 200 meV.3.

Figure 22:
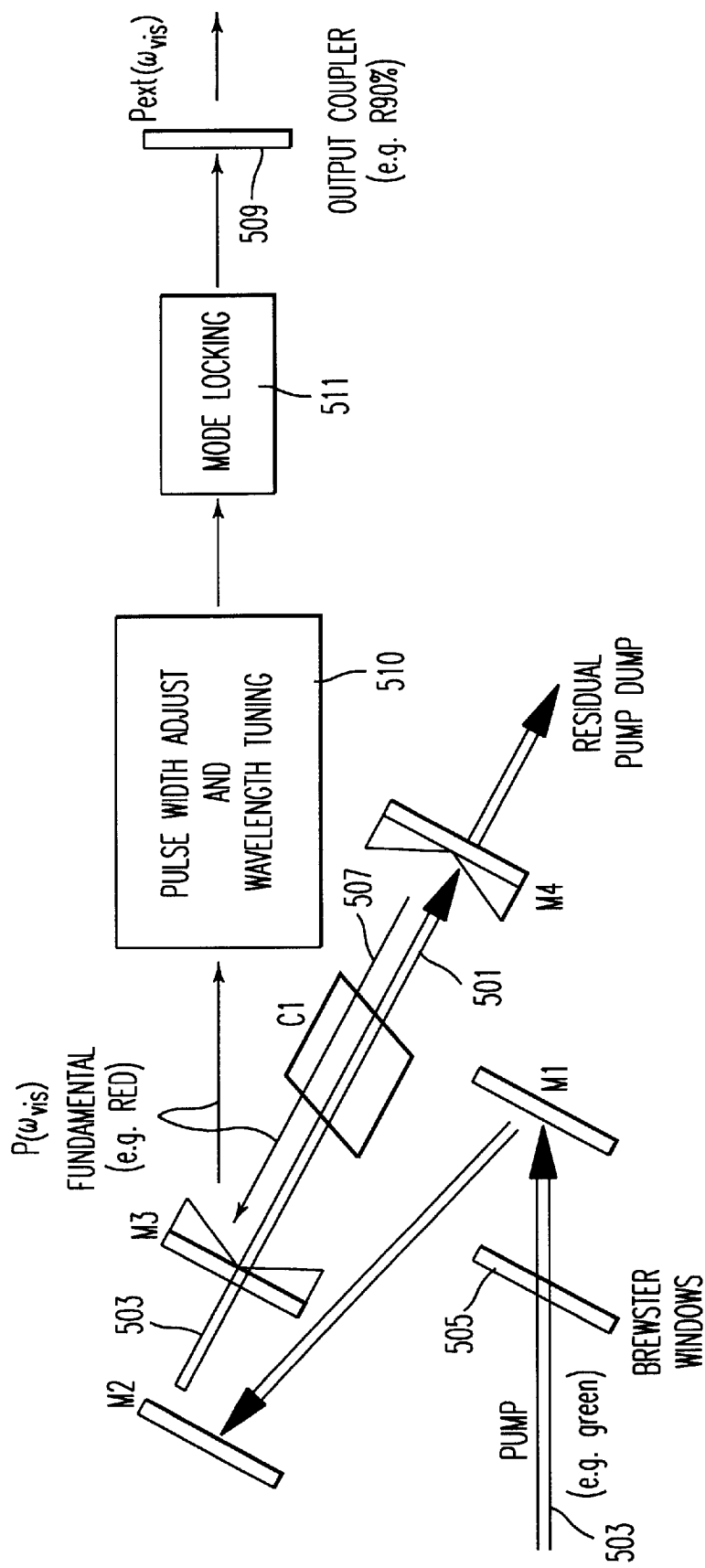
FIG. 22 is a schematic of a mode locked pulse laser.

FIG. 22 shows a conventional pulsed laser e.g. here the schematic of a pulsed laser based on a Ti:Sapphire crystal C1 as the lasing medium. (Examples of alternative crystals to Ti:Sapphire include Cr:LiSaF and Cr:LiSGaF:Cr:YAG and Cr:Fosterite. Alternatively, a cavity based upon optical fibres is also possible). The laser crystal C1 is housed in laser cavity 501 which is defined by dichoric mirror M4 at one end and output coupler 509 at the other end, A pump beam 503 is directed on to said laser crystal C1. The pump beam 503 excites transitions within the laser crystal C1 which then emits a coherent light beam, the input beam, 507. The input beam 507 is reflected back onto the crystal C1 by dichoric mirrors M3, M4 and the output coupler 509, to excite further transitions within the crystal C1 and the crystal C1 emits further coherent radiation at the input beam 7 frequency $\omega_{vis}$.

The pump beam 503 is transmitted through Brewster window 505 and steered via steering mirrors M1, M2 into laser cavity 501 defined by mirror M4 and output coupler 509. The pump beam 503 can pass through mirrors M3 and M4 and is not reflected by them. The input beam 507, produced by the crystal C1 is reflected back onto the crystal via mirrors M3, M4 and the output coupler 509. Other mirrors may also appear in the cavity 501 to steer and focus the beam through the various optical components in the path of the input beam 507, In this example, the pump beam 503 is green and the input beam is red. Mirror M3 is positioned such that it steers the input beam 507 between the crystal C1 and the rest of the lasing cavity 511, terminating on the far side by the output coupler 509 and on the near side by the mirror M4.

The output coupler 509 has a reflectivity between 90 and 100%, the exact value is dictated by the particular application of the invention. For imaging systems which can cope with moderately enhanced levels of THz radiation at $\omega_{THz}$ and also require an output at $\omega_{vis}$ for the reference beam, R is best kept near 90%. For applications where having the maximum amount of THz power is required, R≈100% is used. In this specific example, R is about 90%. This means that 90% of the light which reaches the output coupler 509, is reflected back into the cavity and 10% of the input beam exits the cavity. This maintains the power within the cavity 501.

Such an output coupler 509 can achieve average output levels of 500 mW and peak powers of 75 kW for the input beam at $\omega_{vis}$. The intra-cavity power (the one way power in the cavity) is of the order of 750 kW (5 watt average power). In electro-optic detection systems used for THz imaging, average power levels of 10 to 100 mW, or less, are typically utilised. Thus, R may be considerably increased, resulting in a larger value intra-cavity power $P(\omega_{vis})$. Hence, enhanced $P(\omega_{THz})$ may be achieved whilst still maintaining a reasonable degree of output power ($\text{pext}(\omega_{vis})$) necessary for electro-optic detection of THz radiation for use in a THz imaging system.

The laser also has mode locking means 511. For example, the means 511 may be an acoustic optic modulator which produces a periodic modulation of the loss in the laser cavity. The frequency of this modulation is half the round trip frequency, $\omega_{rt}$ of the laser cavity defined by $$c/2L,$$

where c is the speed of light and L is the cavity length. This produces a stable train of pulses from the laser at $\omega_{rt}$. Those skilled in the art will be aware of alternative mode locking configurations that could be used.

Positive group velocity dispersion effects in the laser cavity results in the temporal broadening or chirping, of the pulses. Pulse width adjustment and wavelength tuning means 510 are provided for the control of the pulse duration by introducing a negative group velocity dispersion in the cavity. One example uses 4 prisms arranged to provide negative group velocity dispersion to the laser cavity pulses, the prisms arranged such that wavelength selection is also possible. An alternative design uses the chirped dielectric mirrors in the cavity, where the mirror coating provides to necessary negative group-velocity dispersion; the mirror coating also determines the lasing wavelength. Following dispersion control, pulse widths ranging from several ps to a few fs are achieved, and typical visible/near-infrared wavelengths over the range 690 to 1,000 nm are possible, typically centred on 800 nm.

Figure 23A:
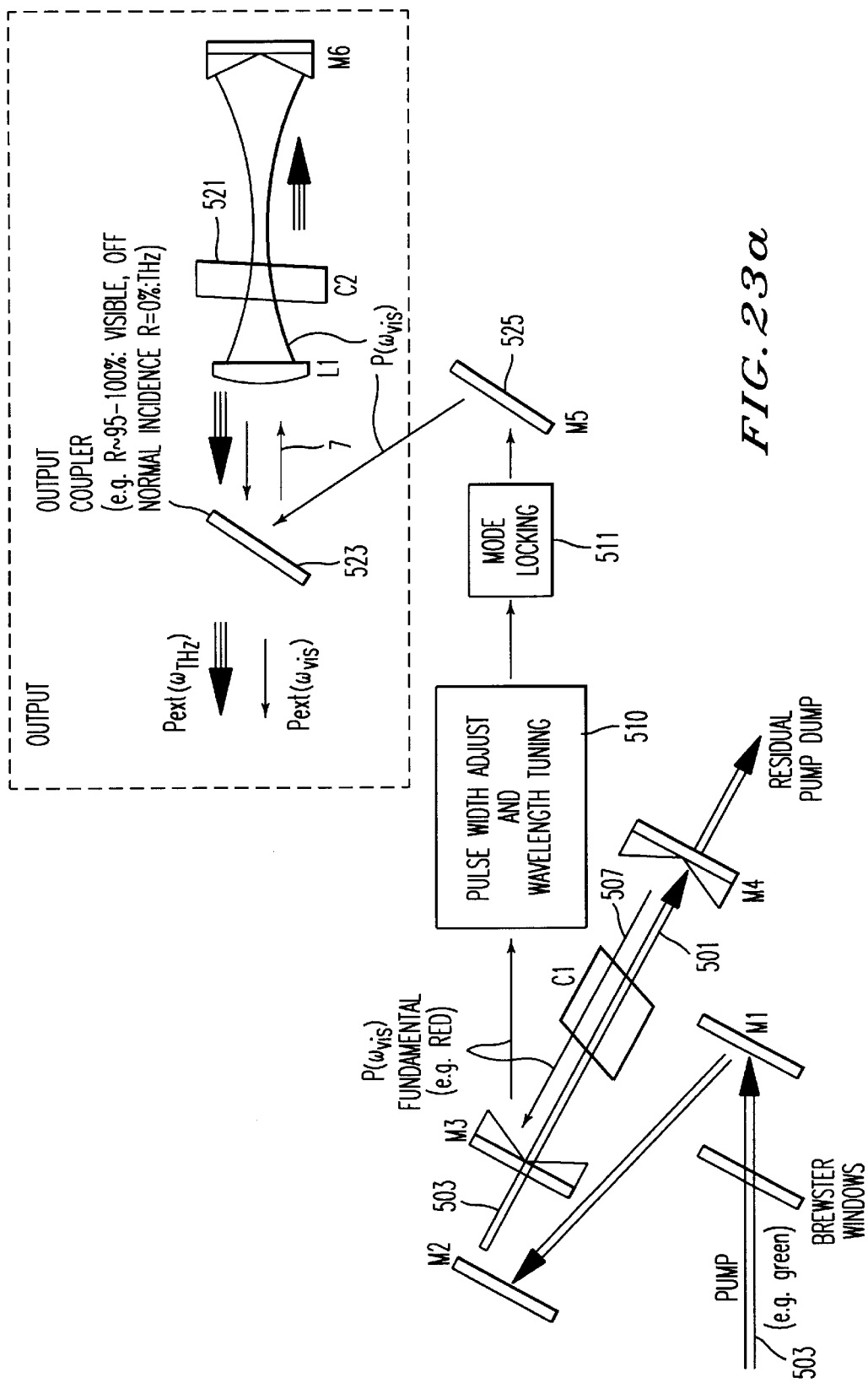
FIGS. 23a, 23b and 23c are radiation sources in accordance with a second aspect of the present invention.

FIG. 23a shows the cavity of FIG. 22 which has been modified to accommodate a frequency conversion member C2. The generation of the coherent input beam 7 from C1, is identical to that described in FIG. 22. Therefore, these details will not be repeated here.

Instead of output coupler 509, a second output coupler 523 is provided. This output coupler has a reflectivity of between 95 and 100% to the input beam 507 and has zero reflectivity but 100% transitivity to the required THz output. The input beam 507 is reflected at normal incidence onto the output coupler 523 via steering mirror 525.

The output coupler reflects input beam 507 onto crystal C2 which is a non linear crystal. The input beam 507 is focused on the crystal C2 via lens L1. The input beam 507 emitted from crystal C1 is reflected in a closed loop defined by mirrors M3, M4, M5, M6 and output coupler 523. Therefore, the cavity keeps reflecting the input beam 507 onto both crystals C1 and C2 and maintains the power within the cavity defined by mirrors M3, M4, M5, M6 and output coupler 523.

The THz radiation emitted from crystal C2 is transmitted via output coupler 523. Output coupler 523 should have zero reflectivity to THz radiation as it is not advisable for THz radiation to be reflected back within the cavity onto crystal C1 and also it is desirable to extract as much THz signal as possible.

The output coupler 523 may be a dichoric mirror which ideally passes radiation at $\omega_{THz}$ unattenuated, while being highly reflective at $\omega_{vis}$ to ensure high $P(\omega_{vis})$ in the cavity.

Possible materials for the output coupler include highly polished silicon or dielectric coated silicon, z-cut quartz with a Ge/Zn/S coating or the like. The angle of incidence may not be parallel to the surface normal for the visible and/or THz radiation. As the THz beam is likely to be much larger in diameter than the visible beam, it may be possible to use a small diameter (<2 mm) silver (or otherwise metallic) layer in the centre of the output coupler with anti-reflection coating, mounted on a z-cut quartz substrate; the silver mirror reflects all the power at the fundamental ($R(\omega_{vis})$ equal 100%) whilst being of a sufficiently small diameter to allow most of the larger THz beam to pass around it ($R(\omega_{THz}) \sim 0\%$).

C2 is a non linear crystal possessing a large second order non linear co-efficient and is configured to emit a frequency which is the difference of two frequency components in the pulsed input beam 507. Here, the crystal is made from ZnTe which has been shown to have a good conversion efficiency for visible wavelengths light to THz frequencies when pumped external to a laser cavity. Thus, average power levels of several $\mu$W in the THz are produced for input power levels of ~300 mW in the visible range at $\omega_{vis}$ for frequency conversion crystals placed external to the cavity. Even higher power levels will be achieved with a crystal inside the cavity.

In order to minimise losses, C2 is cut at the Brewster's angle for the polarisation and frequency of the visible radiation $\omega_{vis1}$ and $\omega_{vis2}$. Alternatively, or in addition to cutting at the Brewster's angle, C2 could be anti-reflection coated to minimise these losses.

ZnTe is a good material for crystal C2 as it has minimum absorption at $\omega_{THz}$ due to mechanisms such as phonon absorption and transparent at 800 nm, the centre wavelength of Ti:Sapphire based ultrafast lasers. Alternatively, GaAs maybe used in conjunction with a pulsed laser source operating at a wavelength where GaAs is transparent, for example Cr:LiSaF, or Cr:YAG could be used for crystal C1.

The length of C2 should also be optimised for the system. Phase matching frequency conversion optimally occurs over the whole length of the crystal. In practice, the useful length is given by the coherence length $l_c$ which is a measure of the distance over which the optically-induced non-linear polarisation and the generated THz electric fields remain in phase. It is defined by:

$$l_c = \pi c/(\omega_{THz}|\eta_{vis} - \eta_{THz}|).$$

Optics L1 and M6 are arranged such that the input beam 507 is focused down on the crystal C2. The alignment of these and other components is such that there is no spatial walk-off of the input and THz beams in the crystal C2. The latter point ensures that high spatial mode quality is ensured and also favours a long interaction length i.e. Full distance $l_c$ is utilised. L1 is anti-reflection coated for $\omega_{vis}$ and as a non-absorbing/non-reflecting as possible as $\omega_{THz}$. Materials such as anti-reflection coated TPX or Z-cut quartz are possible candidates for dichoric, transmissive optics such as L1.

Figure 23B:
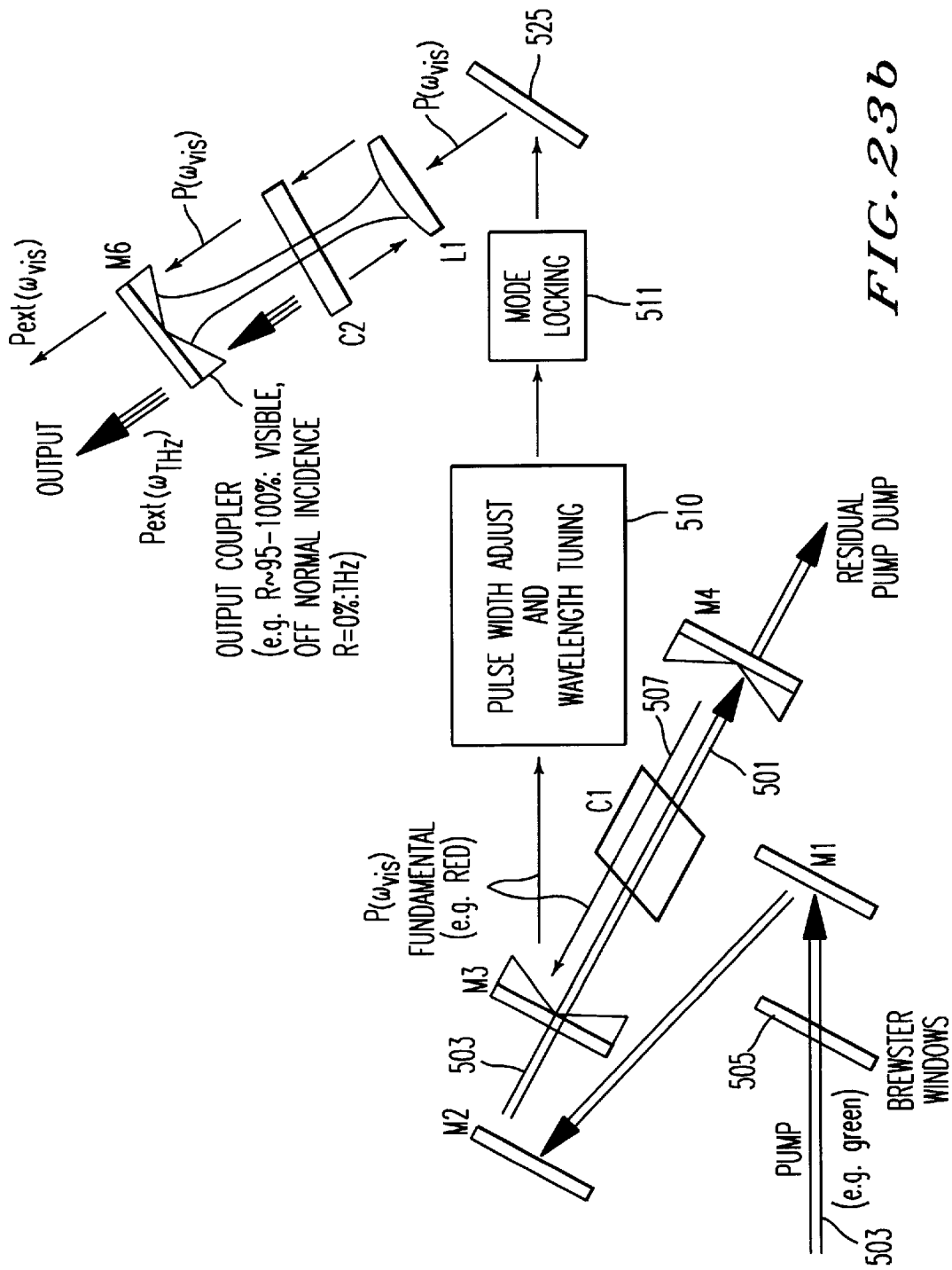

FIG. 23b shows a variation of the source of FIG. 23a. Mirror M6 is used as the output coupler, removing the requirement for output coupler 523 of FIG. 23a. This causes the outputted THz pulse to be generated by the visible pulse on its first pass through C2.

In FIG. 23a, two THz pulses are generated by the visible pulse during the two passes it makes through C2. These pulses may, in some cases, destructively interfere thus reducing the efficiency of the THz generator. The design of FIG. 23b addresses this problem. Further, the THz pulse only passes through mirror M6 (i.e. a single element) before leaving the cavity thus reducing dispersion and absorption effects at $\omega_{THz}$.

Figure 23C:
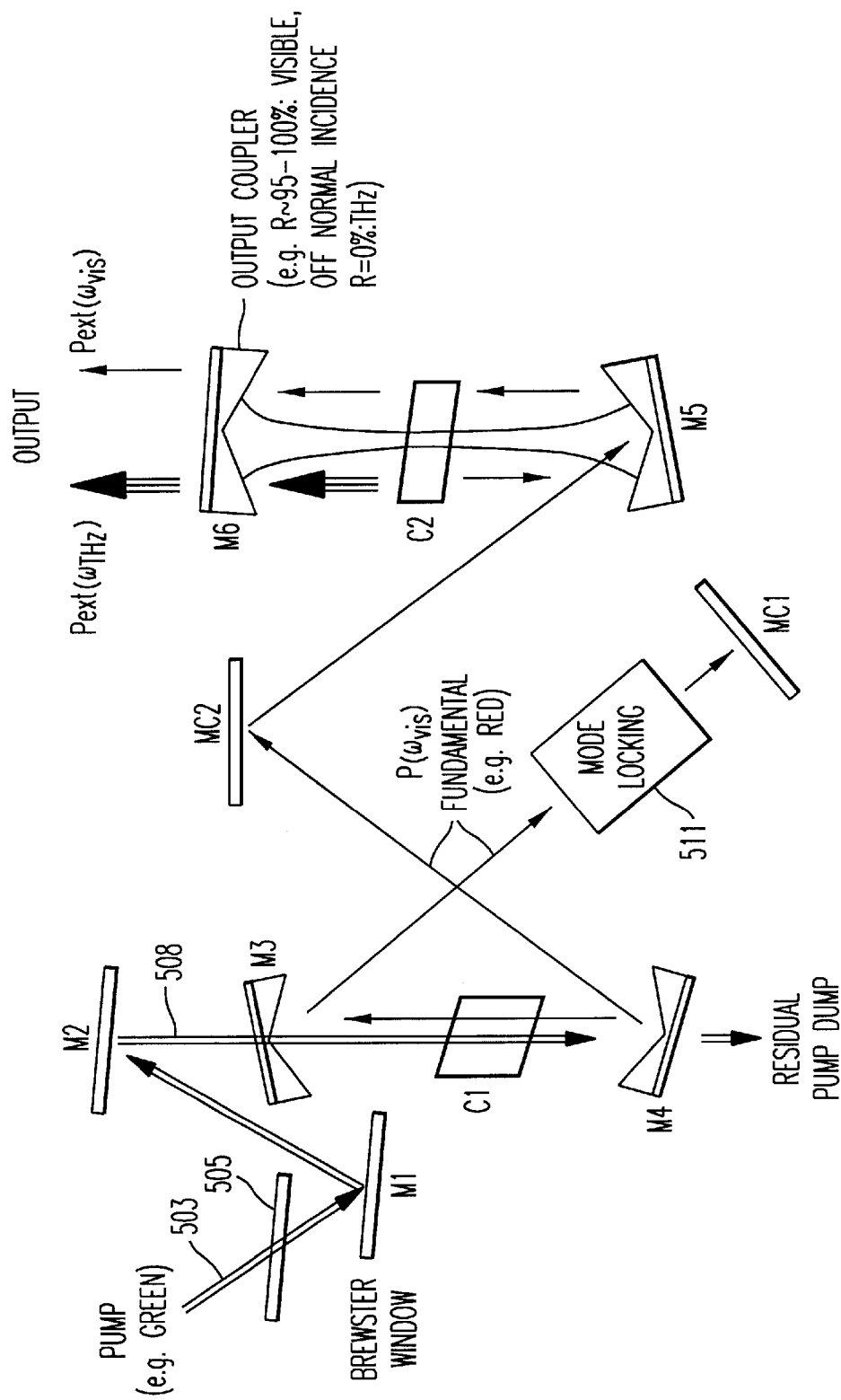

FIG. 23c shows a further modification of the design in FIGS. 23a and 23b. This design uses chirped dielectric mirrors MC1 and MC2 in the cavity 1 to control the pulse dispersion/length and the wavelength, thus removing the need for the pulse length adjustment means 510 of FIG. 23a. In FIG. 23c, mirrors MC1 and MC2 have chirped dielectric coatings to produce the negative group velocity dispersion required to shorten the pulses. The mode locking means 511 is still required.

In FIGS. 23a to 23c, two frequencies are provided by beam 507. This irradicates the problems caused by using two separate beams. For example in V Petrov and F. Seifert Optic letters, 19, 40–42 (1994). Here, two pulsed lasers are used and problems are encountered due to non-optimised beam overlap due to the fact that the two beams at $\omega_{vis1}$ and $\omega_{vis2}$ are of different origin, i.e. not part of the same beam. This design also suffers because one of the beams (e.g. $\omega_{vis1}$) is not of intra-cavity origin and hence the power available at $\omega_{vis1}$ is greatly reduced, causing a corresponding drop in the power of the difference frequency radiation.

This THz source can be used in a THz imaging system. For example, the type of system shown in FIG. 13. The system of FIG. 13 can be simplified into three main sections, a generator 531, an imaging section 533 and a detection section 575. THz radiation is generated in the generating section 533 by using a THz emitter which is supplied by a visible pulsed laser 537. The am can be generated using the THz source described in relation to FIGS. 23a, 23b and 23c.

Figure 24:
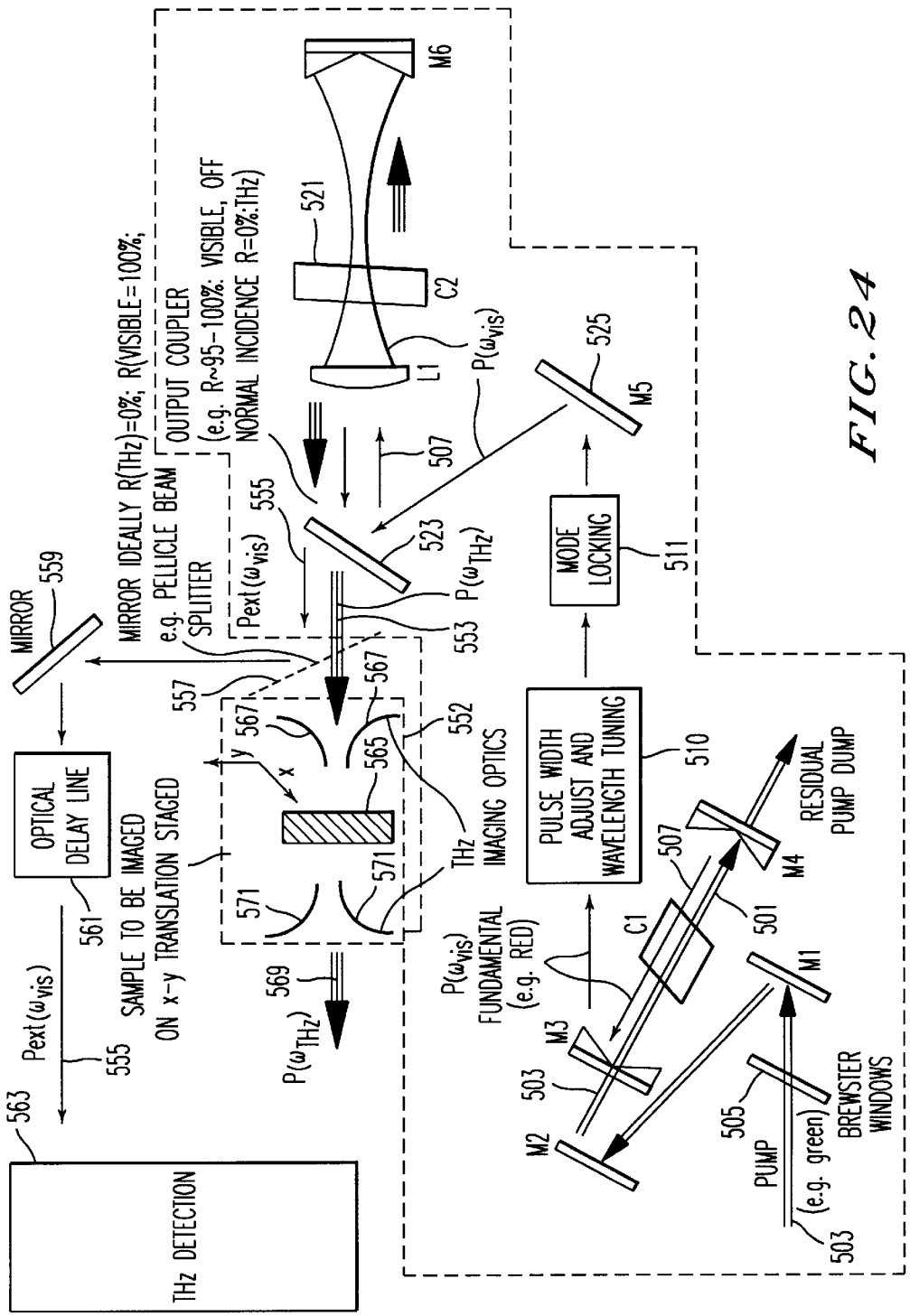
FIG. 24 is an imaging system in accordance with a second aspect of the present invention.

An imaging system in accordance with an embodiment of the present invention will be described with reference to FIG. 24. Here, for simplicity, details of the detection part of the system will be omitted. These have already been described with reference to FIG. 12.

The THz generation section is indicated by the components within box 51. The individual components of the generation system 551 have been described with reference to FIGS. 23a, 23b and 23c. Therefore, the details of these will be omitted from the description of FIG. 24. The imaging system requires both a visible light pulse and a THz pulse to be emitted from the generation section 551. Therefore, the output coupler 23 should not 100% reflective to visible radiation to allow some visible radiation to be emitted from the THz generation section 551.

The emitted THz beam 553 and visible 555 from the generation system are incident on beam splitter 557. This beam splitter 557 allows transmission of the THz beam 553 but reflects the visible light beam 555 onto mirror 559 which reflects the beam 55 into optical delay line 561. The delayed beam 555 is then inputted into the THz detection unit 563.

The THz beam 553 is directed into the imaging section 552 and onto sample 565 via THz imaging optics 567. The sample 565 is located on a motorised X-Y translation stage (not shown) so that the whole sample 565 can be imaged. (The x-y plane is othogonal to the beam axis). The THz radiation 569 carrying the imaging information from the sample is reflected into the THz detection system 563 via THz imaging optics 571.

The presence of visible radiation 555 as well as THz radiation 569 allows for imaging and electro-optic detection to be performed inside a single nitrogen-purged unit.

The sample 565 is mounted on a X-Y motorised translation stage (not shown) which is controlled by a PC computer (not shown). Each section (pixel) of the object may then be imaged. To improve the spatial resolution of the technique, off-axis parabolic mirrors, condenser cones, and lenses may be used to focus the beam to a diffraction limit spot. By mounting the sample in the near field of a condenser cone, the diffraction limit may be overcome and spatial resolution of about 50 $\mu$m may be achieved. The imaging system can function with or without such objects depending on the nature of the object to be imaged and the nature of the detection circuit. These variations on the imaging section will be discussed with reference to FIGS. 25 to 28.

Figure 25:
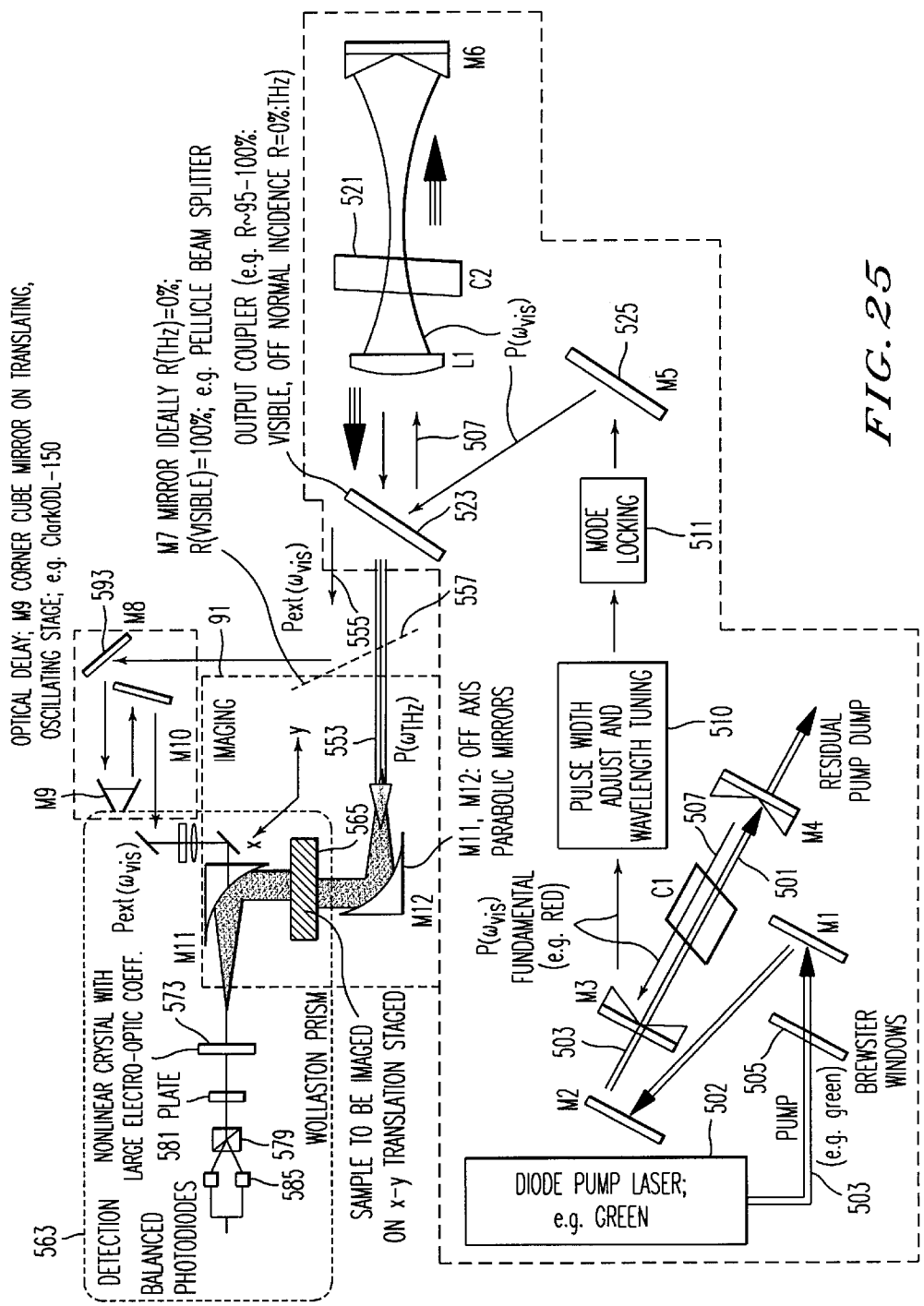
FIG. 25 shows the imaging system of FIG. 24 with the detection system of FIG. 12.

FIG. 25 shows a complete THz imaging system. The individual components of the detection section 563 and the THz generation section 551 have been described with reference to FIGS. 23a, 23b, 23c and FIG. 12, and discussion of them will not be repeated here.

All of the items shown in FIG. 25 sit on an optical bread board of dimensions 36 inches by 36 inches. The only external units required are a power supply for the diode laser and a cooling unit for the generation section 551.

The imaging section 591, has a motorised stage which is movable in the x-y plane, i.e. along two orthogonal axis which are perpendicular to the incident beam of THz radiation.

The imaging section 591 has two mirrors M11 and M12. Mirror M12 directs the THz beam 553 onto the sample 565. Mirror M11 is positioned to reflect the THz radiation transmitted through sample 565 onto the detection crystal 573. Mirrors M11 and M12 are off axis parabolic (OAP) mirrors. Such mirrors are configured so that the phase difference between the incident and reflected beams is the same at all points on the mirror. The parameters resulting in an off axis parabolic surface are characterised by the focal length of the mirror.

An optical delay section 593 is also shown. The visible light beam emitted from the generating section is reflected by beamsplitter 557 into delay section 593. The delay section 593 has a corner cube mirror M9 which is moveable along the beam axis. The beam is directed onto corner cube mirror M9 via mirror M8. The beam is reflected off corner cube mirror M9 onto mirror M10. Corner cube mirror M9 is oscillated back and forth along the beam direction with an oscillation frequency of several 10 s of Hz. This increases or decreases the path length of the visible beam 555 as required. A Clark ODL-150 system may be used to drive the mirror, this is capable of delays of 150 ps. The emitted beam is then combined with the emitted THz beam at mirror M11. Alternatively the THz and visible beams may be combined colinearly using a beam splitter, for example, a pellicle beam splitter. Such a device would be placed before or after M11 and would eliminate the requirement for a hole in M11.

Figure 26:
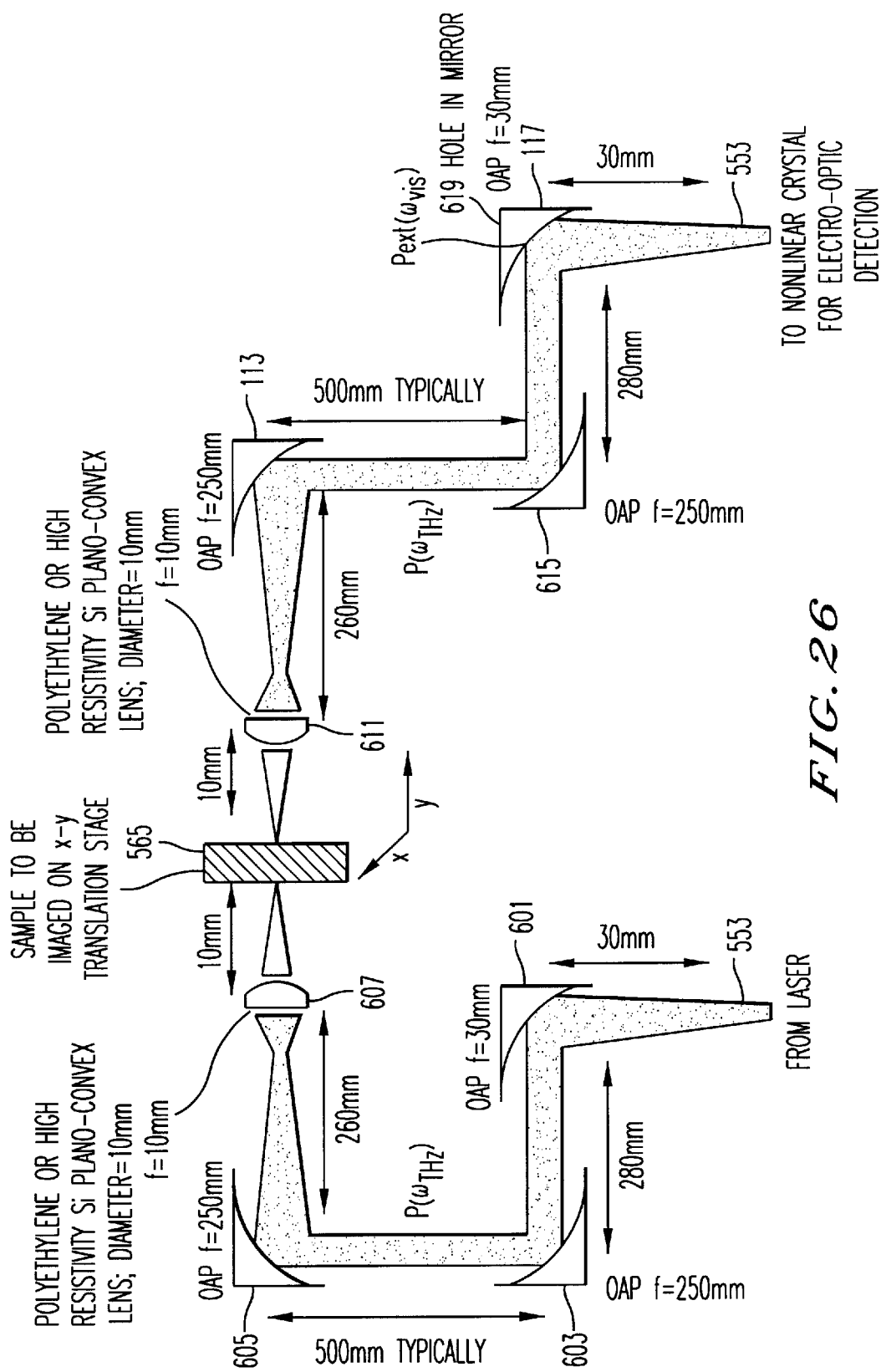
FIG. 26 shows a variation on the imaging section of FIG. 25.

FIG. 26 shows a variation on the imaging section 591 of FIG. 25. The extended path length over which the THz beam 553 travels is purged with nitrogen to remove water vapour and hence improve the quality of the image.

Due to diffraction effects associated with the large wavelengths in the THz range, the cross-sectional size of the THz beam 553 and imagine applications is not sufficiently large that it may be treated as plain parallel. If diffraction effects are such that the radiation is paraxial so that it can be represented by a scalar field distribution, Gaussian beam mode optics and optical techniques can be used. The simplest case for system design is to assume that the fundamental mode dominates the beam profile. The use of Gaussian mode optics and design applied to conventional THz radiation and systems (generated in the Fourier transform machines, far-infrared lasers or Gunn diodes) is applicable and important to THz imaging systems.

A number of design rules or guidelines should be followed when constructing a THz imaging system to obtain a good quality image. For transmission optics such as lenses, geometric losses are kept to a minimum by ensuring that the ratio of the lens thickness to focal length and diameter to focal length is less than 0.2. If this is satisfied, then losses in the lenses will be primarily due to absorption and reflection. In this case, choice of materials is important.

A requirement which arises in pulsed systems is the need for the material to be non-dispersive so that pulse broadening does not occur. Given these requirements, high density polyethylene (DHPE), polytetrafluorethylene (PTFE), high resistivity silicon (Si), and TPX are some of the best materials and can also be machined in a lathe, any material combining low absorption and low dispersion at THz frequencies is a good candidate for fabrication of transmission optics, provided its shape can be suitably fabricated for a lens. Reflection losses in lenses tend to be highly frequency dependent at THz frequencies. Therefore care must be taken in lens design to ensure that all frequencies across the pulse bandwidth undergo the same reflection (and absorption) losses.

Ideally, reflective optics (mirrors) are used wherever possible instead of transmission optics (lenses) in order to minimise a number of losses associated with transmission optics, which include (i) frequency-dependent reflection losses and amplitude pattern distortion at dielectric (e.g. air-lens) interfaces, (ii) frequency-dependent absorption losses, (iii) diffraction effects and distortions to field distribution due to power falling on the lens's surface at an angle.

An additional property of importance in imaging (and not particular to Gaussian mode beam optics) is that if two mirrors are separated by the sum of their focal lengths, then the size of the beam waist (minimum beam diameter in plane normal to optical axis) on the optical axis after the reflection from the second mirror will be frequency-independent. This is true of the last mirror (focusing element) in a chain provided there are an even number of focusing elements in the chain. This provides a major advantage for THz imaging as the pulse is comprised of a wide range of frequency components, and it is desired to keep the object at a fixed position on the optical axis whilst images are being recorded at various (x, y) points and at all THz frequencies in the pulse. This is particularly important THz imaging as the spectral coverage (bandwidth) of THz pulses increases into the mid-infrared and even higher frequencies.

The system in FIG. 26 will produce beams with l/e diameters (for the fundamental Gaussian mode in the beam) of 1–2 mm at the sample in the THz frequency range (e.g. at 300 GHz, diameter=2 mm). In the system of FIG. 26, six mirrors and two lenses are used as opposed to the two mirrors of FIG. 25. The direction of the beam in FIG. 26 is reversed to that in FIG. 25. In the imaging section, the beam is first reflected off first OAP mirror 101 onto second OAP mirror 103 and then onto third OAP mirror 105. Second 103 and third OAP mirrors each have a focal length of 250 nm. They are separated by 500 nm.

The beam is reflected from the third OAP mirror 605 onto plano-convex lens 607 which has a focal length of 10 mm and a diameter of 10 mm. Third OAP mirror 605 is separated from piano convex lens 607 by 260 nm (i.e. the sum of their focal lengths). The lens 607 is made from polyethylene or high resistivity Si. The lens 607 is placed 10 mm from the motorised stage (not shown) on which sample 609 is mounted. The beam has traversed through an even number of focusing optics and mirrors (601, 603, 605 and 607) which are all spaced apart by the sum of their focal lengths. Hence, the waist of the beam at the sample is independent of the frequency. Here, the beam diameter is chosen to be 2 mm, independent of frequency in the frequency range of about 300 GHz (0.30 THz).

Once the beam has passed through sample 565, the transmitted THz radiation falls onto second piano convex lens 611. Piano convex lenses 607 and 611 are identical in optical characteristics. Lens 611 focuses the THz radiation onto the fourth OAP mirror 613. Fourth OAP mirror 613 has a focal length of 250 mm and reflects the THz beam onto fifth OAP mirror 615. Fifth OAP mirror 615 also has a focal length of 250 mm and lies 500 nm away from the fourth OAP mirror 613 (i.e. the sum of the focal length of the fourth and fifth OAP mirrors).

The beam is reflected from the fifth OAP mirror 615 to the sixth OAP mirror 617. Sixth OAP mirror has a focal length of 30 mm and is located 280 mm away from the fifth OAP mirror (i.e. the sum of the focal length of the fifth and sixth OAP mirrors).

The sixth OAP mirror 617 is provided with a hole 619. The visible light beam 555 is passed through this hole to combine it with the THz beam 569 for detection.

Figure 27:
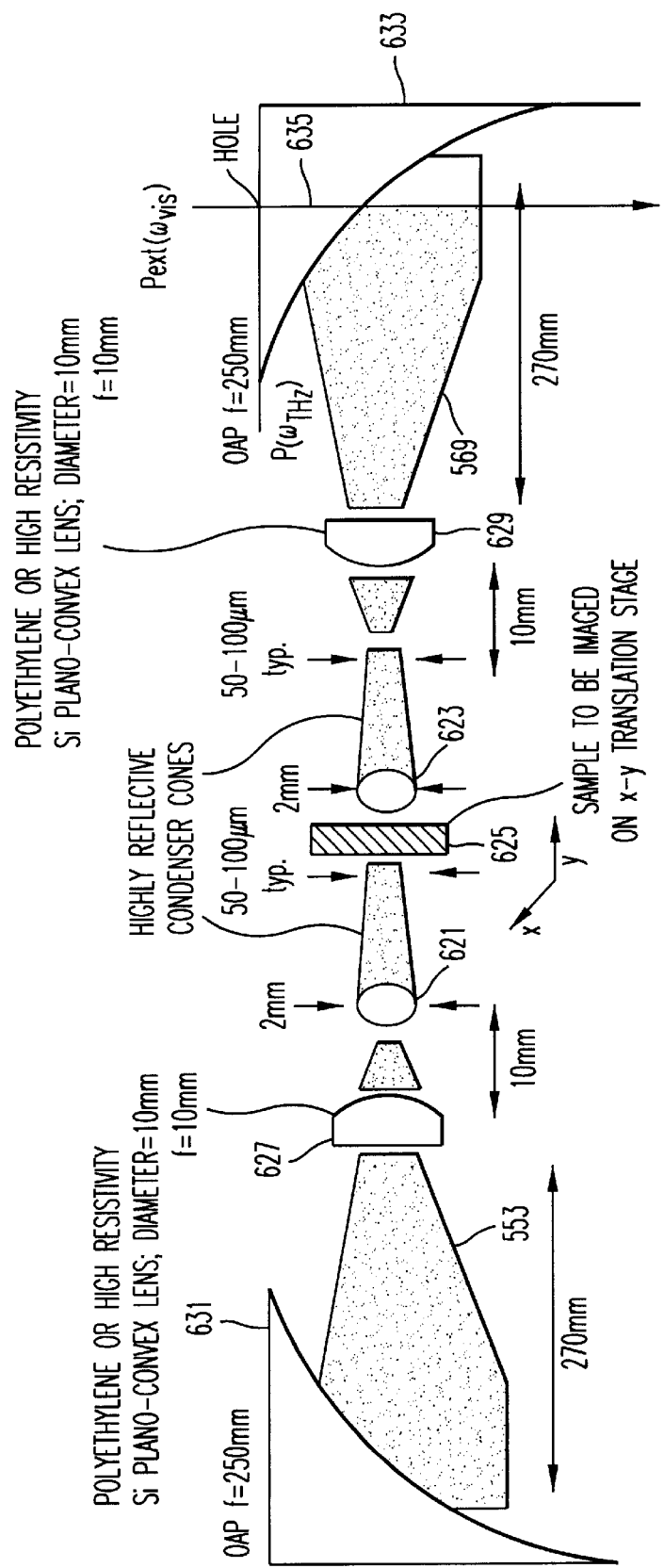
FIG. 27 shows a variation on the imaging section of FIG. 25.

Further improvements in spatial resolution may be achieved by inserting condenser cones (made of brass or copper, highly polished on insides, with electro-plating and/or gold/silver evaporated coating) adjacent to the sample to be imaged as shown in FIG. 27. In FIG. 27, condenser cones 621 and 623 are located on either side of the sample 125 between the sample 625 and piano convex lenses 627 and 629 respectively. The piano convex lenses are the same as those described with reference to FIG. 26. They have a focal length of 10 mm and are placed 10 mm away from condenser cones 621 and 623. The cones have a typical entrance aperture of 2 mm and an exit aperture of between 50 to 100 µm.

The sample 625, is typically placed within a few wavelengths of the exit aperture of condenser cone 621 e.g. about 100 µm, such that near field imaging techniques may be used to realise THz spot sizes at the sample which are less than the diffraction-limited spot size.

Another advantage of this design is that the beam waist size is frequency independent at the aperture entrance, so that all frequencies in the pulse should fit into the condenser cone.

The plano-convex lenses 627, 629 condenser cones 623, 621 and sample 625 are placed between OAP mirrors 631, 633. The mirrors have a focal length of 250 mm. THz beam 553 is reflected from OAP mirror 631 onto piano convex lens 627 which focuses beam 653 onto condenser cone 621. The beam 553 enters through the widest aperture of the condenser cone and exits through the narrowest aperture onto sample 625. Once beam 553 has passed through sample 625 it enters condenser cone 623 and exits the condenser cone 623 through its narrowest aperture onto piano convex lens 629. The beam is then reflected off OAP mirror 633 onto the detection crystal 573. The OAP mirror 633 has a hole 635. Visible light from the generator is combined with the THz beam 569 at mirror 633. It should be noted also that the optical configuration in FIG. 27 can also be used with a multiplicity of other mirrors, such as the arrangement in FIG. 26. It should be noted, however, that a variety of different focal lengths are possible for mirrors 633 and 631.

Also, the arrangement of condenser cones used here can easily be inserted into the system of FIG. 26 using similar guidelines to beam size and mirror placement as those already elucidated.

Figure 28:
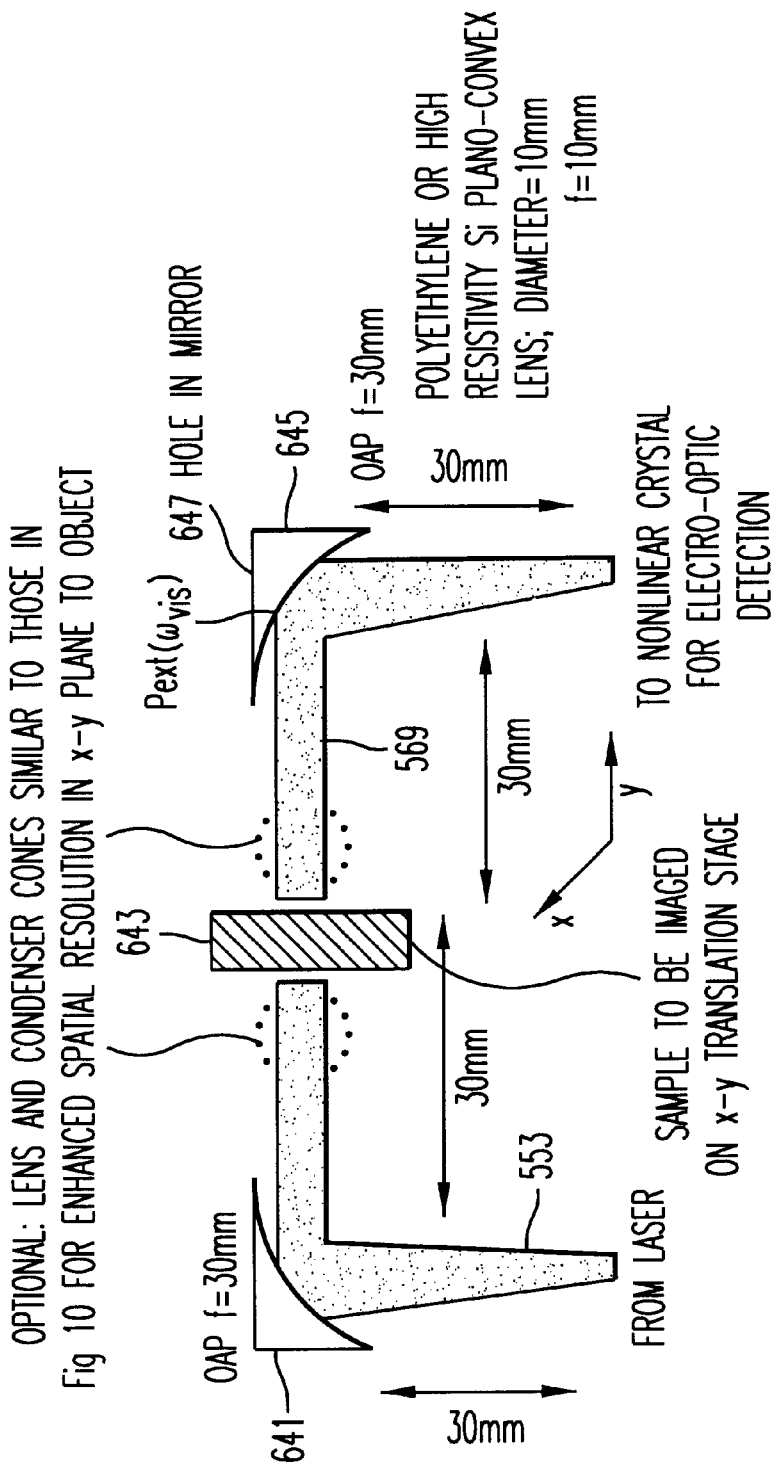
FIG. 28 shows a variation on the imaging section of FIG. 25.

It should be noted that simpler coupling systems such as that in FIG. 28 are possible which utilise only two off-axis parabolic mirrors. These reduce the path length of the beam and therefore minimise losses due to any water vapour or other absorbing cases in the beam path. However, transmission optics are necessary in order to create frequency independent beam waists at the same and/or to realise higher spatial resolution.

In FIG. 28, the THz beam 553 is reflected from OAP mirror 641 onto sample 643. The focal length of OAP mirror 641 is 30 mm and sample 643 is placed 30 mm away from OAP mirror 641. Optionally, further optical components such as lenses and condenser cones as described in FIG. 27 may be added between mirror 564 and sample 643.

Once beam 553 has passed through sample 643 it is encoded with imaging information and is referred to as beam 569, Beam 569 is reflected from OAP mirror 645 onto the detection crystal. The OAP mirror is provided with a hole 647 which allows the visible beam 555 to be mixed with the THz beam 569 for detection.

Figure 29:
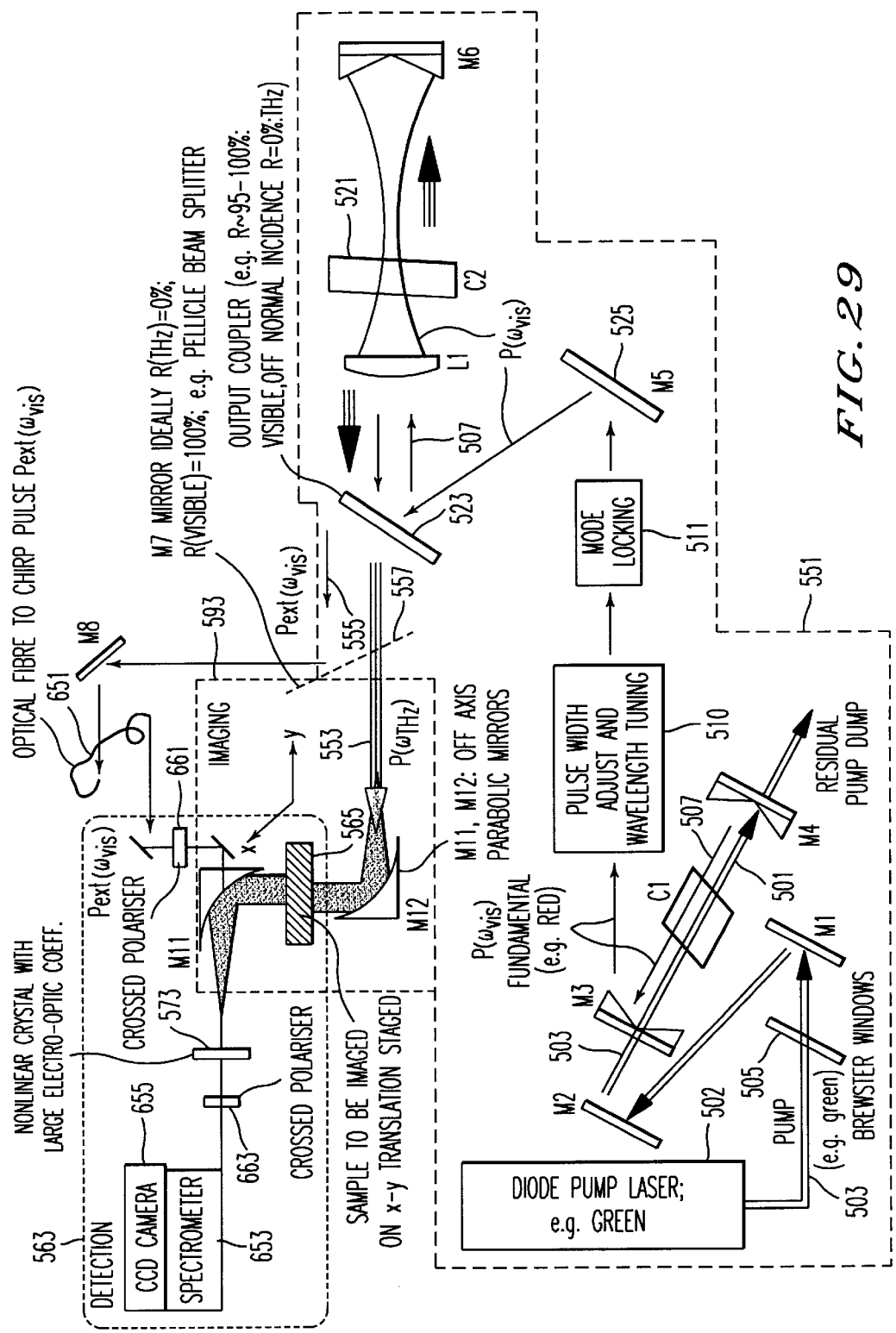
FIG. 29 shows a further embodiment of an imaging system in accordance with the third aspect of the present invention.

FIG. 29 shows a further example of an imaging system. The generation and imaging sections have been described with reference to FIGS. 23a, 23b, 23c, 24 and 25 to 28. The details of these components will not be repeated here. In FIG. 29, the delay section of FIG. 25 is replaced with a grating pair or an optical fibre 651 which chirps the visible pulse, extending its temporal width from 50 fs to about 20 ps. The different wavelength components in the visible pulse travel through the detection crystal 573 at different times.

Thus, when a grating spectrometer 653 is used to spatially disperse the wavelengths and a CCD camera 655 is used to record the spatial diversion, each pixel in the (for example) X-direction corresponds to a different wavelength and hence a different time. The result is that a given row of pixels in the x-direction on the CCD 655 effectively map out the temporal form of the THz beam which co-propagates through the detector crystal 573 and rotates the polarisation of the visible beam at different times during the pulse by varying amounts. Thus, transmission through the object being imaged is plotted as a function of time along one direction in the CCD array. Hence, the rotation of the polarisation of the reference beam 555, is measured by crossed polarises 661, 663 which are arranged on either side of the detection crystal 573.

The imaged object may then be stepped in the y direction on the translation stage in the usual way to develop a 2D THz image. Alternatively, if the probe beam is focused down by a cylindrical lens to a line (say 400 μm in x by 10 mm in y) on the sample, the THz transmission along the y axis of the sample can be measured by the pixels along y direction of the CCD, i.e. the y-pixels of the CCD may then be used to image the object in the y-direction without resorting to the translation stage moving in y. A full image is then completed by stepping the translation stage in x. Both of these abilities (to measure time delay along the x-axis of the CCD and y image information without mechanical movement) resulting in much quicker acquisition times if sufficient THz power is available as in this intra-cavity design to affect higher signal to noise ratios. Quicker data acquisition and potentially cheaper cost for more compact systems are the result.

The primary advantage of this system is the fast data acquisition owing to the lack of moving parts such as translation stages; using this system, both a) imaging along the y-direction of the object and b) the sampling of the time domain is very fast, limited the creation of a time delay are very fast, limited only by the speed of the CCD camera and the need to average many frames from the camera to get adequate signal to noise rations (SNR) on the images. The latter is the chief mechanism which limits the application of this technique, and hence the realisation of real-time imaging. Poor SNR results in part from the fact that the balanced photodiode detection scheme outlined in FIG. 12 can no longer be used because the quarter wave plate would introduce background light onto the CCD as strong as one-half of the total probe power. Small signal detection in this scenario will be overwhelmed by photon shot noise if a CCD camera is used. To reduce the "ambient" light level on the camera, crossed polarizers are used in which the signal on the CCD falls to zero in the absence of a THz electric field. Such as detection system is optimal for a CCD, but still does not provide as high signal-to-noise as the system in FIG. 12, especially if lock-in detection is used in the latter case.

To overcome this SNR problem, regenerative amplifiers are used (not shown) to boost the optical peak power which nonlinearly generates the THz pulse, resulting in a larger THz field. Such a system suffers, however, from numerous disadvantages. Regenerative amplifiers are extremely expensive (~£100K) and tend to be large and bulky. Also, a second pump laser to drive the amplifier is required. Lastly, such systems operate at low repetition rates (50 Hz–250 kHz), resulting in a relative decrease in average power The bright intracavity sources designed here would overcome all of these disadvantages. The intracavity design could therefore be a major step forward in the realisation of a THz imaging system with sufficiently quick data acquisition at sufficiently high signal to noise ratios to realise THz images at video frame rates (~38 frames/sec), so-called "THz movies".

Figure 30:
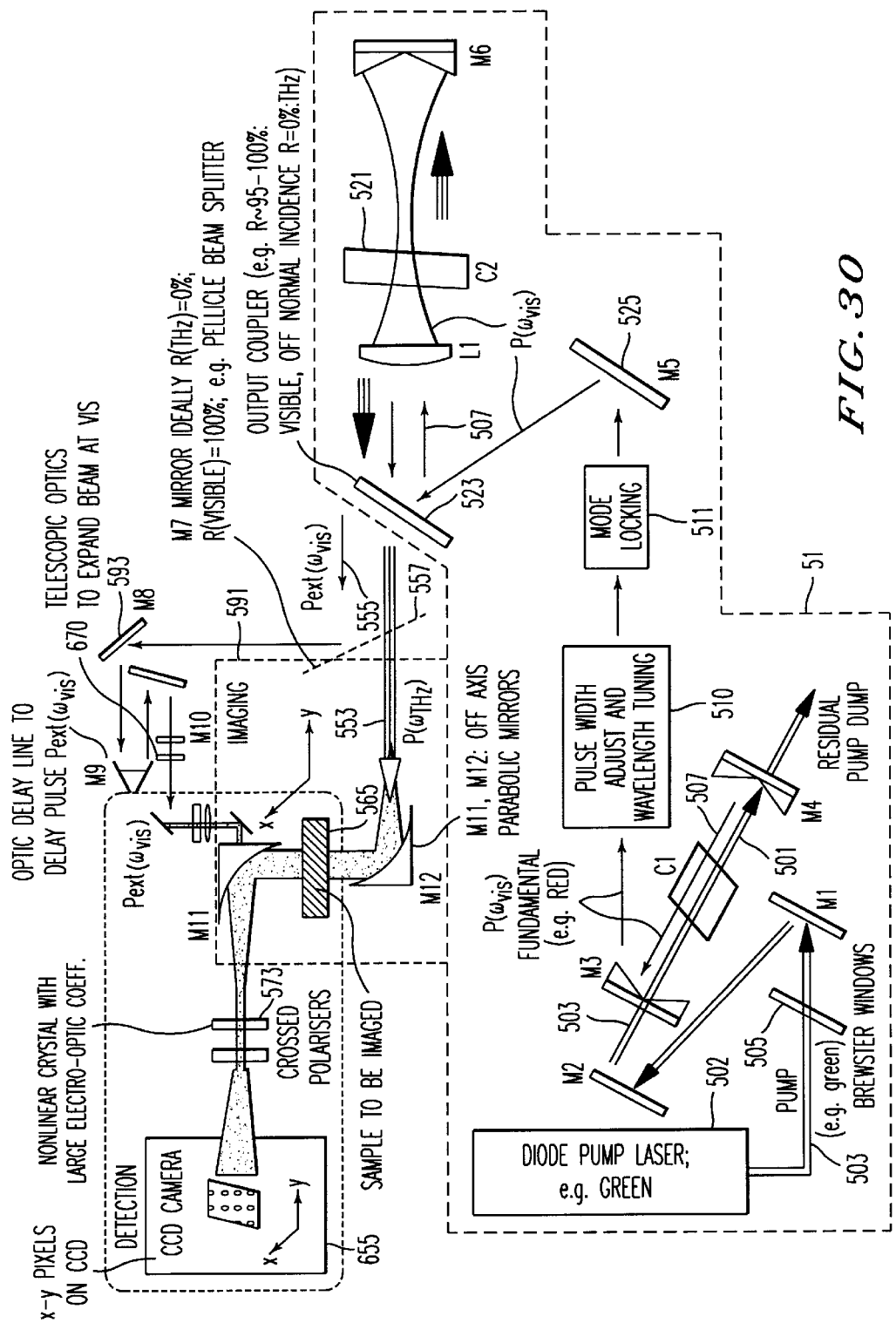
FIG. 30 shows another example of an imaging system in accordance with the third aspect of the present invention.

FIG. 30 shows a further example of the imaging system of FIG. 29. In FIG. 30, the motorised stage (of FIG. 30) is redundant. Instead, the imaging area of the CCD camera 655 is matched to the imaging area of the detection crystal 573. This area is typically several mm². The reference beam 555 is expanded by optics 670 (e.g. telescopic or analogous optics), such that the reference beam has a larger cross sectional area than the THz beam and ideally fills all the pixels in the CCD camera 655. The distribution of the rotated polarisation of the reference beam in the x-y plane (proportional to the THz power transmitted through the sample 565 in the x-y plane) is transferred to the pixels of the CCD camera, resulting in a THz image of the object appearing on a CCD or a computer screen (not shown) attached to the output of CCD camera 655. The time delay in this system is created by an optical delay line (as described with reference to FIG. 25). This is the only mechanical moving part of the system.

Figure 31:
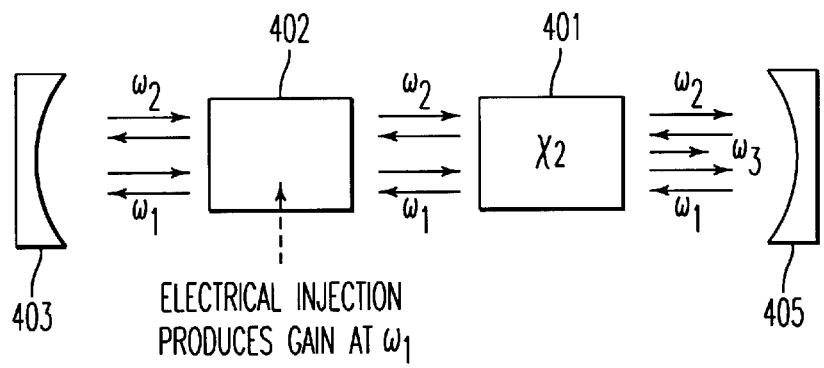
FIG. 31 shows a schematic of an optical parametric oscillator situated within the same cavity as its driving laser.

FIG. 31 shows a variation on FIG. 19. Here, the phased matched material (401) is arranged intra cavity i.e. within the cavity of the laser 402. In this case, both the material producing gain at the pump frequency $\omega_1$ and also the non-linear material, are placed inside the highly reflecting mirrors 403, 405 of the laser cavity. The cavity mirrors 403, 405 are designed to be highly reflecting at both the pump frequency $\omega_1$ and the signal frequency $\omega_2$. They therefore support a strong oscillating field at both frequencies.

Figure 32:
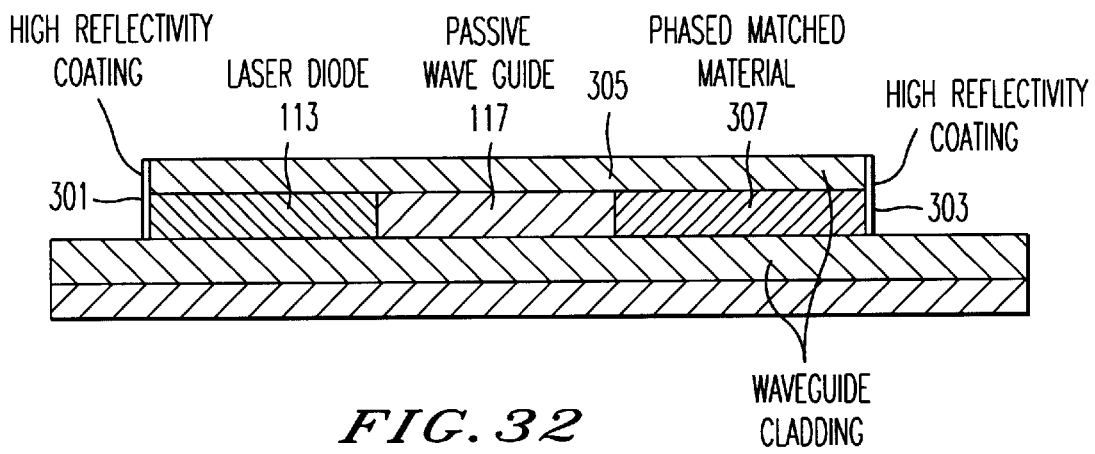
FIG. 32 shows an intracavity optical parametric oscillator.

FIG. 32 shows an example of an intracavity optical parametric oscillator, where mirrors 301, 303 are placed on either side of a non-linear material 305 which is phase matched 307 for optical parametric generation. The mirrors 301, 303 are designed to be highly reflective at frequency $\omega_2$. In this device there is an enhancement of the optical field at frequency $\omega_2$. The mirrors 301, 303 can be fabricated by coating the ends of the non-linear material 305 with a dielectric thin film coating. Alternatively the mirrors 301, 303 can be fabricated using another photonic bandgap material.

In the device of FIG. 32, the phase matched region is integrated with a semiconductor laser diode on the same substrate, as shown schematically in FIGS. 16 and 17. Such integrated architectures allow cheaper fabrication and assembly and are more compact.

What is claimed is:

1. An optical device comprising:
    an optical modulation region which comprises phase matching means for enhancing the phase matching between at least two different frequency signals propagating in the optical modulation region in response to illumination by at least one incident beam of radiation, the phase matching means having a spatial variation in its refractive index along a component of the incident radiation beam configured to maximise a distance in the modulation region over which the at least two different frequency signals stay in phase.

2. An optical device comprising:
    an optical modulation region which comprises phase matching means for enhancing the phase matching between at least two different frequency signals propagating in the optical modulation region in response to illumination by at least one incident beam of radiation, the phase matching means having a spatial variation in its refractive index along a component of the incident radiation beam configured to maximise a distance in the modulation region over which the at least two different frequency signals stay in phase,
    the modulation region further comprising frequency conversion means for emitting a beam with an emitted radiation frequency in response to illumination by the at least one input beam, the emitted beam having a different frequency to that of the or an incident beam;
    the phase matching means enhancing the phase matching between the polarisation generated by the or an incident beam and the emitted beam.

3. The optical device of claim 2, wherein said optical modulation region is configured to emit a beam with a frequency substantially equal to the difference in frequency between two incident beams.

4. The optical device of claim 2, wherein the device is configured to emit radiation within the range of 100 GHz to 20 THz.

5. The optical device of claim 2, wherein the optical modulation region is configured to emit a beam with a frequency substantially equal to that of the sum of the frequency of two incident beams.

6. The optical device of claim 2, wherein the optical modulation region is configured to emit a beam with a frequency different to that of the frequency of a single incident beam.

7. The optical device of claim 2, wherein the optical modulation region is configured to emit a beam with a frequency substantially equal to that of an integer multiple of the frequency of a single incident beam.

8. The optical device of claim 1, wherein the modulation region is configured to rotate the polarisation vector of a first input beam in response to illumination with a second input beam and emit the beam with the rotated polarisation vector.

9. The optical device of claim 1, wherein the variation in the refractive index of the phase matching region is generally parallel to a component of the or an incident beam.

10. The optical device of claim 1, wherein the variation in the refractive index is substantially periodic.

11. The optical device of claim 1, wherein the variation in the refractive index is periodic, the pitch of the periodic variation in the refractive index is between 100 nm and 10 $\mu$m.

12. The optical device of claim 1, wherein the optical modulation region comprises one or more selected from $LiIO_3$, $NH_4H_2PO_4$, ADP, $KH_2PO_4$, $KH_2ASO_4$, Quartz, $AlPO_4$, ZnO, CdS, GaP, GaAs, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, DAST (4-N-methylstilbazolium) or Si.

13. The optical device of claim 1, wherein the optical modulation region is arranged within a waveguide structure.

14. The optical device of claim 1, wherein optical modulation region comprises a first cladding layer, a second cladding layer, and a core layer, the core layer being interposed between the first and second cladding layers.

15. The optical device of claim 1, wherein the modulation region has one or more holes formed in the path of the beam.

16. The optical device of claim 1, wherein the modulation region has one or more holes formed in the path of the beam, and said holes are not formed in a cladding layer.

17. The optical device of claim 1, further comprising one or more cladding layers,
wherein the modulation region has one or more holes formed in the path of the beam and said holes are formed in at least one cladding layer.

18. The optical device of claim 1, further comprising a diode laser as a source for the incident radiation.

19. The optical device of claim 1, further comprising two diode lasers as the source for the incident radiation.

20. The optical device of claim 1, further comprising a pulsed laser as the source of incident radiation.

21. The optical device of claim 1, wherein the optical modulation region is located within a mirror cavity.

22. The optical device of claim 1, wherein the at least one incident beam of radiation is produced within a lasing cavity and said optical modulation region is located within the said cavity.

23. A radiation source comprising:
a frequency conversion member for emitting a beam of radiation in response to irradiation by a pulsed input beam having a plurality of frequency components, the emitted beam having a frequency different to that of the frequency components of the pulsed input beam,
the pulsed input beam being produced within a lasing cavity and said frequency conversion member being located within said lasing cavity.

24. The radiation source of claim 23, wherein the frequency conversion member is an optically non-linear member.

25. The radiation source of claim 23, wherein the frequency conversion member is configured to emit radiation with a frequency substantially equal to the difference between two frequency components of the pulsed input beam.

26. The radiation source of claim 23, wherein the frequency conversion member is configured to emit radiation with a frequency of between 100 GHz to 20 THz.

27. The radiation source of claim 23, further comprising an output coupler capable of transmitting the emitted beam and reflecting the pulsed input beam, the output coupler being positioned on an opposing side of the frequency conversion member to the side which the pulsed input beam first enters the frequency conversion member.

28. The radiation source of claim 23, wherein the source is configured to emit both the beam emitted from the frequency conversion member and the pulsed input beam.

29. The radiation source of claim 23, wherein the pulsed input beam has a pulse width of between 10 ps to 10 fs.

30. The radiation source of claim 23, wherein the frequency conversion member comprises at least one of the following $LiIO_3$, $NH_4H_2PO_4$, ADP, $KH_2$, $A_5O_4$, Quartz, $AlPO_4$, ZnO, CdS, GaP, GaAs, $BaTiO_3$, $LiTaO_3$, $LiNbO_3$, Te, Se, ZnTe, ZnSe, $Ba2NaNb_5O1_5$, $AgAsS_3$, proustite, Cd, Se, CdSe, $CdGeAs_2$, $AgGaSe_2$, $AgSbS_3$, ZenS, BBO, KTP, DAST (4-N-methylstillbazolium), $L_4NbO_3$.

31. The radiation source of claim 23, wherein the frequency conversion member is crystalline and is cleaved at its Brewster angle for one of the frequency components of the input beam or beams.

32. The radiation source of claim 23, wherein the frequency conversion member has an anti-reflection coating, provided to reduce reflections at a frequency component of the pulsed input beam.

33. The radiation source of claim 23, wherein an element is provided to stop the emitted beam irradiating the lasing element.

34. The radiation source of claim 23, wherein an output coupler is provided which is capable of transmitting the emitted beam and reflecting the pulsed input beam.

35. The radiation source of claim 23, further comprising an output coupler capable of transmitting the emitted beam and reflecting the pulsed input beam, the output coupler having substantially 0% reflectivity to the emitted beam and between 90 and 100% reflectivity to the pulsed input beam.

36. A radiation source comprising:
a frequency conversion member for emitting a beam of radiation in response to irradiation by one or more input beams, the emitted beam having a frequency substantially equal to the difference between two frequency components of the one or more input beams, the one or more input beams all being produced within a lasing cavity and said frequency conversion member being located within said cavity.

37. An imaging system comprising a radiation source for supplying a beam of imaging radiation onto an object and a detector, the radiation source comprising a frequency conversion member for emitting a beam of radiation in response to irradiation by a pulsed input beam having a plurality of frequency components, the emitted beam having a frequency different to that of the components of the pulsed input beam, the pulsed input beam being produced within a lasting cavity and said frequency conversion member being located within said lasing cavity.

38. The imaging system of claim 37, wherein the system further comprises lenses made from one or more of the following: high density polyethylene (HDPE), polytetrafluoroethylene (PTFE) or high resistivity Silicon.

39. The imaging system of claim 37, comprising a motorised stage for supporting an object which is to be imaged.

40. The imaging system of claim 37, wherein the imaging radiation is directed onto the sample by at least one off axis parabolic mirror.

41. The imaging system of claim 37, wherein the imaging radiation is directed onto the sample by an even number of off axis parabolic mirrors arranged with each adjacent pair of mirrors separated at the sum of the focal lengths of the two mirrors.

42. The imaging system of claim 37, wherein the system further comprises a condenser cone.

43. An imaging system comprising a radiation source for supplying a beam of imaging radiation onto an object and a detector, the radiation source comprising a frequency conversion member for emitting a beam of radiation in response to irradiation by one or more input beams, the emitted beam having a frequency different to that of the one or more input beams, the one or more input beams all being produced within a lasing cavity and said frequency conversion member being located within said lasing cavity, the detector comprising a non-linear crystal, wherein said imaging radiation is detected by the non-linear crystal using a reference beam with a different wavelength to that emitted by the frequency conversion member.

44. The imaging system of claim 43, the system further comprising a CCD camera with a detection area similar to that of the cross sectional area of the reference beam.

45. The imaging system of claim 43, wherein the reference beam corresponds to one or more of the input beams.

46. The imaging system of claim 45, wherein the non-linear crystal is configured to rotate the plane of polarisation of the reference beam in the presence of the imaging radiation.

47. The imaging system of claim 46, wherein the rotation of the polarisation is detected by two crossed polarizers located on either side of the non-linear crystal.

48. The imaging system of claim 44 further comprising a mirror which can be oscillated to increase or decrease the optical path of the reference beam.

49. The imaging system of claim 43, comprising a grating pair to increase the pulse width of the reference beam.

50. The imaging system of claim 43, comprising an optical fibre to increase the pulse width of the reference beam.

51. The imaging system of claim 43, wherein the imaging system further comprises a grating spectrometer.

52. The imaging system of claim 43, further comprising a CCD camera.

53. The imaging system of claim 43, wherein optical elements are provided to increase the reference beam cross sectional area to be larger than the cross sectional area of the imaging radiation at the detector crystal.

54. A radiation source comprising:

a frequency conversion member for emitting a beam of radiation in response to irradiation by one or more input beams, the emitted beam having a frequency different to that of the one or more input beams, the one or more input beams all being produced within a lasing cavity and said frequency conversion member being located within said lasing cavity, the source further comprising an output coupler which is capable of transmitting the emitted beam and reflecting the input beam or beams.

55. The radiation source of claim 54, the output coupler having substantially 0% reflectively to the emitted beam and between 90 and 100% reflectively to the input beam or beams.

56. The radiation of claim 54, wherein the output coupler is positioned on an opposing side of the frequency conversion member to the side which the input beam or beams first enters the frequency conversion member.

* * * * *